United States Patent [19]
Wise et al.

[11] Patent Number: 5,981,833
[45] Date of Patent: Nov. 9, 1999

[54] NUCLEAR RESTORER GENES FOR HYBRID SEED PRODUCTION

[75] Inventors: Roger P. Wise; Patrick S. Schnable, both of Ames, Iowa

[73] Assignees: Iowa State University Research Foundation, Inc., Ames, Iowa; The United States of America as represented by the Secretary of Agriculture, Washington, D.C.

[21] Appl. No.: 08/794,494

[22] Filed: Feb. 4, 1997

Related U.S. Application Data

[63] Continuation-in-part of application No. 08/346,611, Nov. 29, 1994, Pat. No. 5,648,242.

[51] Int. Cl.⁶ .............................. A01H 5/00; A01H 1/00; C12M 15/00; C12M 15/82
[52] U.S. Cl. ..................... 800/271; 800/303; 800/275; 800/298; 536/24.1; 536/24.33; 536/23.6; 435/412; 435/235.1
[58] Field of Search ...................................... 800/271, 288, 800/303, 275; 435/412, 424, 430, 430.1, 235.1; 536/24.1, 24.33, 23.6

[56] References Cited

U.S. PATENT DOCUMENTS 4,751,347   6/1988   Erickson ..................................... 47/58

FOREIGN PATENT DOCUMENTS

WO 90/08831   8/1990   WIPO.

OTHER PUBLICATIONS

Wright et al. Isolation and Characterization of male flower cDNA's from maize. The Plant Journal 3. (1) 41–49.
MPSRCH analysis of NDA sequence, 1993.
Aarts et al., *Nature,* 363, 715–717 (1993).
Albertsen et al., *Can. J. Genet, Cytol.,* 23, 195–208 (1981).
Bailey–Serres et al., *Theor. Appl. Genet.,* 73, 252–260 (1986).
Braun et al., *Plant Cell,* 2, 153–161 (1990).
Dewey et al., *Proc. Nat'l. Acad. Sci. USA,* 84, 5374–5378 (1987).
Dixon et al., *Theor. Appl. Genet.,* 63, 75–80 (1982).
Forde et al., *Proc. Nat'l. Acad. Sci. USA,* 75, 3841–3845 (1978).
Huang et al., *EMBOJ,* 9, 339–247 (1990).
Janska et al., *Genetics,* 135, 869–879 (1993).
Kamps, T., et al., *Maize Genet. Coop. Newsl.,* 66, 45 (1992).
Kennell et al., *Mol. Gen. Genet.,* 210, 399–406 (1987).
Korth et al., *Proc. Nat'l. Acad. Sci. USA.,* 88, 10865–10869 (1991).
Laughnan et al., *Ann. Rev. Genet.,* 17, 27–48 (1983).
Laver, et al., *The Plant Journal,* 1, 185–193 (1991).
Levings, *Plant Cell,* 5, 1285–1290 (1993).
Levings, et al., *Cell,* 56, 171–179 (1989).
Mann et al., *Theor. Appl. Genet.,* 78, 293–297 (1989).
Mariani et al., *Nature,* 347, 737–741 (1990).
Nivison et al., *Plant Cell,* 1, 1121–1130 (1989).
Poehlman, *Breeding Field Crops,* pp. 139–142 (1987).
Pring et al., *Genetics,* 89, 121–136 (1978).
Pring et al., *Ann. Rev. Phytopathol.,* 27, 483–502 (1989).
Rongnoparut et al., *Gene,* 101, 261–265 (1991).
Schardl et al., *Cell,* 43, 361–368 (1985).
Schnable et al., *Genetics,* 136, 1171–1185 (1994).
Singh et al., *Plant Cell,* 3, 1349–1362 (1991).
Sisco, *Crop Sci.,* 31, 1263–1266 (1991).
Wise et al., *Proc. Nat'l. Acad. Sci. USA,* 84, 2858–286 (1987a).
Wise et al., *Plant Mol. Biol.,* 9, 121–126 (1987b).
Wise et al., *Theor. Appl. Genet.,* 88, 785–795 (1994).

*Primary Examiner*—Gary Benzion
*Attorney, Agent, or Firm*—Leydig, Volt & Mayer, Ltd.

[57]   ABSTRACT

The present invention relates to the field of producing hybrid seeds, and specifically relates to the application of certain cloned nuclear fertility restorer genes, which restore male fertility to cytoplasmic male-sterile plants. In particular, the present invention relates to an enriched or substantially isolated nucleic acid sequence comprising a nucleotide sequence that hybridizes at least under moderately stringent conditions to SEQ ID NOS: 1, 3 or 4 and restores male fertility to a cytoplasmic male-sterile plant; a vector comprising such a sequence; an organism, virus, seed, plant cell, and plant comprising such a vector; methods for the production of hybrid seed; a method of producing a variant of a cytoplasmic male-sterile plant, and a method of suppressing cytoplasmic male sterility, all of which make use of the aforementioned nucleic acid sequences.

26 Claims, 4 Drawing Sheets

| | | | | | | | | | | | | |
|---|---|---|---|---|---|---|---|---|---|---|---|---|
| maize Rf8 | C U A U U U G G C U | C A A C U C U | C C G A G U U A | (+123 to +147 of T-urf13) |
| maize Rf* | A G U U A G C C A A | C C A C A A U | A G A G U G G A | (+143 to +167 of T-urf13) |
| maize Rf1 | U C A A U G A U C A | C U A C U U U | C U U A A A C C | (-3 to +22 of T-urf13) |
| sorghum Rf3 | U G U U G U C U U A | C U A C A A U | A C C G C U C G | (+179 to +204 of orf107) |
| archaea 23S | U A C U A G G U A G | C C A C A U U | A U A G C C G U | (+1662 to +1686 of 23S pre-rRNA) |
| maize rrn26 | C G C U C A U G U U | C G A C G C U | A U C G A A A A | (-23 to +2 of 26S rRNA) |
| rice atp9 | C G C U C A U G U U | C G A C G C U | A U U A U G G A | (-110 to -86 of atp9) |

FIG. 1

```
Rf1 cDNA       1468   KVQRIMTQPINLIFRFLQSKARIQIW   1545
                      KVQ++M QPINLIFR+LQ+++RIQ+W
Human snRNP       9   KVQKVMVQPINLIFRYLQNRSRIQVW     34
```

FIG. 4

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 402 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
CTTTTCCTCT TCTGATGTAT GCCTGGAAAG TTGGCCCTGC TTTGGCATGT GGAAATACTC      60

TCGTGCTCAA GACTGCTGAA CAAACCCCTC TATCGGNTTT GTATATCTCC AAATTGTTGC     120

ATGAGGCTGG ACTACCTGAG GGTGTTGTGA ATGTCGTTTC TGGTTTTGGN CCTACTGCTG     180

GTGCTGCTCT TGCTAGTCAC ATGGATGTTG ATAAGATCGC ATTTACTGGA TCTACCGATA     240

CTGGAAAAAT TATTCTCGAG TTGGCTGCAA AGAGCAACCT TAAGACAGTG ACACTGGAGT     300

TAGGAGGAAA GTCCCCTTTC ATCATATGGA CGAAGCTGAT GTTTGGACCA GCTNTTGGAG     360

CTTGNGCANC TTGGCCTGTN CTTTTACCAG GANAATGCTG TA                        402
```

(2) INFORMATION FOR SEQ ID NO:2:

(i) SEQUENCE CHARACTERISTICS:
       (A) LENGTH: 133 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Phe Pro Leu Leu Met Tyr Ala Trp Lys Val Gly Pro Ala Leu Ala Cys
1               5                   10                  15

Gly Asn Thr Leu Val Leu Lys Thr Ala Glu Gln Thr Pro Leu Ser Xaa
            20                  25                  30

Leu Tyr Ile Ser Lys Leu Leu His Glu Ala Gly Leu Pro Glu Gly Val
        35                  40                  45

Val Asn Val Val Ser Gly Phe Gly Pro Thr Ala Gly Ala Ala Leu Ala
    50                  55                  60

Ser His Met Asp Val Asp Lys Ile Ala Phe Thr Gly Ser Thr Asp Thr
65                  70                  75                  80

Gly Lys Ile Ile Leu Glu Leu Ala Ala Lys Ser Asn Leu Lys Thr Val
                85                  90                  95

Thr Leu Glu Leu Gly Gly Lys Ser Pro Phe Ile Ile Trp Thr Lys Leu
            100                 105                 110

Met Phe Gly Pro Ala Xaa Gly Ala Xaa Ala Xaa Trp Pro Val Leu Leu
        115                 120                 125

Pro Gly Xaa Cys Cys
    130
```

(2) INFORMATION FOR SEQ ID NO:3:

(i) SEQUENCE CHARACTERISTICS:
       (A) LENGTH: 402 base pairs
       (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO:3:

```
CTTTTCCTCT TCTGATGTAT GCCTGGAAAG TTGGCCCTGC TTTGGCATGT GGAAATACTC        60

TCGTGCTCAA GACTGCTGAA CAAACCCCTC TATCGGCTTT GTATATCTCC AAATTGTTGC       120

ATGAGGCTGG ACTACCTGAG GGTGTTGTGA ATGTCGTTTC TGGTTTTGGN CCTACTGCTG       180

GTGCTGCTCT TGCTAGTCAC ATGGATGTTG ATAAGATCGC ATTTACTGGA TCTACCGATA       240

CTGGAAAAAT TATTCTCGAG TTGGCTGCAA AGAGCAACCT TAAGACAGTG ACACTGGAGT       300

TAGGAGGAAA GTCCCCTTTC ATCATATGGA CGAAGCTGAT GTTTGGACCA GCTGTTGGAG       360

CTTGNGCANC TTGGCCTGTN CTTTTACCAG GANAATGCTG TA                          402
```

(2) INFORMATION FOR SEQ ID NO:4:

(i) SEQUENCE CHARACTERISTICS:
        (A) LENGTH: 2473 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
GAACAATTGT TACAATGAGA TTTTAAAGTT ATTAGGAGAT GTGCTCCCAA AGCCCAATAA        60

GTTGCCTAAA GACATGTACC AATCAAAGAC AATTATCAAA GGTCTCGGTA TGGATTATGA       120

GAAGATTGAT GCGTGCAAAA ATAATTGTAT GCTTTTCATG AAGGAGCATG CGGAAGAGAA       180

AAAATGTCTG AAATGTGGAC AATCTAGATT TGTGGAAGTT GTTAATGATG AGGGTGAGAA       240

GGTGATGACA GAAATCGACA TAGACAGCGC CATCAGCAGG ACGAGGACGA TGATGAGGTC       300

GTAGTCAACC ATACCTATGG GGTTGATGGA CACATTCGGT TGGCTAAGCG AATGGAGGCT       360

CAAACTGGAG TTGTCCCGAG CCCAATCGAT GTTTATAGGA GAGGGCATCG AGCGAAAAAC       420

AGTGAAATCT CCGATGAGCT GTGTAGTCAA GCGGCCGTTG AGCGTATGGA GACATACGAG       480

CAGGAGATGG TTAAGAAGTA TGGAGAAGAC TACGATTGGC GAGGAGCGCC TACCATCGAC       540

GCTGAGGTTG TGCATTCACT TGGCGGCAAG GCGCATGGAC GATATTTCTA TGTTAACCGG       600

TGTTATCGAT TCGACGGAGT TGCGTTCTCG TGGCGGCTCT TCGTCGCAGG CGGGCTGTGG       660

TAGTAGCAGC CGTAGTCGCC GCTCTGTATC TAGCATGGAG GAAGCTATGA GGGAGCAGCA       720

AGAAAAGTTT CGTGAAGAGA TGCGGCAACA ACAAATGGCA TTTCTCCAAC AGCAATCAGA       780

GTACATGGCT GCTTACAACG CACAGGCGCA ACAAGCAATG AACTCTTGGT TCCACAGCA       840

GGCACAGCAG CAACCATTTG TTTTCCCTCA ATTTCAGCCG CCGATGCCTC AGTGGGGATT       900

ACATGCTCCG CCACCTCCAC CTCCACCTCA GGGATCCGGG GTCATGGGCC ACAACACGCC       960

ACCACCGGTC ATACCAGCAC CAGGAGCTTA TGCAGGGGAG GGAGCTTATG CAGGGGAGGG      1020

AGCTTATGCA GGAGAGGATC CAACCCCGTT ACACGACTTC GTCGACCAGT TATTGGCTTC      1080

TGGAGGTAGT GGACACAACT CCAACGACCC CAATGTGTGA TTAAGTTAGC TTTGTGTCGC      1140

ACTGTGTTGT AATGAACTAT TTTGTGGACT TTATGTTTGT ATGGACTATT TGTGGACTTT      1200

ATATTTGTAT GGACTCAAGT TTTAGGTTGT GAACTCAAGT ATAAATTTTC TGTGATTGCA      1260

AAAAAAAAAA AAAAAAAAAA AAAAGCGGCC GCGTCGACTG CTCAGCTCAG GGCGAAACAA      1320

AACCCTCCTC CCTCACTGCC CCCTCGCAGA CGAGACGCGT GGTAGCTAGG GTTTTGGCCT      1380
```

-continued

```
CGCCGCGCAC GCCTCCTGAA GCTTCTAGAC GTTCGAGGAG GAGGAGGGGA GGCTCCCGCC      1440

GCCGCCGCCG CAGCCATGGC GTCCACCAAG GTGCAGCGTA TCATGACCCA GCCCATCAAC      1500

CTCATCTTCC GTTTCCTCCA GAGCAAAGCG CGCATCCAGA TCTGGGATAG AGCAAGGCCA      1560

CACACACACA CACACACACC ACTAGTAGGC TAGCCTAGCC TTTTAGTCGT CGAGGAGGAG      1620

CAAGAAGGGC GCGCACGCAA GCAGGCAAGC AAGAAGAGAG CCGATCGACC GAGAGCTAGC      1680

ACGCGATGGC GAGGTCTTCC AAGATGATGG TGGCGGCAGC TCTGCTGGCC TTGGCCCTGG      1740

CCGTGTCGAC CGCCGAGGCG AGGAACATCA AGACCACGAC GACGGAGAAG AAGGACGACG      1800

CGGTGGTGCA GCCGCAGACC TTCCCGCCCT TCGACCGCCT CGGCGGCGGC GCGTCCCCGG      1860

CGTTCGGCGG CCTCCCCGGC GGCAGCATTC CTGGCAGCAG CATTCCCGGG TTCAGCATGC      1920

CCGGCAGCGG CAGCAGCCTA CCCGGGTTCA GCTTGCCCGG CAGCGGCAGC ATGCCCCTCT      1980

TCGGCGGCGG CTCCCCGGGC TTCAGCGGCT TCGGCGGCAT GCCCGGGTCG CCCACCGCCG      2040

GCTCCGTCCC CGAGCACGCC AACAAGCCCT GAACGCCAAC AAGCGTGGTA GTAGAGTGGT      2100

GCTACTGTTA CTGTAGTACG TCGTCGTCTT CATGCATGCG TGGTTCGTGG TTTCCCCTAG      2160

CTCCATACGA GCAGTAGTTG GGCCTTGCAC GTACCGTACG TCTAGCTAGC TATATATATA      2220

TAGCTTGTGT TCTACTGCTT TTTAGTTTAA TTACCTGCCT GCATTGGAGA GTTGGATCTG      2280

TTTCATTTGG TGGTGTTTGC TTTACTATTA GGTCAGTATC TGTTTGTGGA GACTTGGTGT      2340

TTAATTTATT TAGCCGTTTG TGACTGGTTG TAGCTAGCGG TGGTGCGGTG GTGATGTTCT      2400

TGAGGCATGA ATAATGCTAC ATGCATGTGA TGTATCCATG TTTTGTGTGT GGTAAAAAAA      2460

AAAAAAAAAA AAA                                                        2473
```

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Lys Val Gln Arg Ile Met Thr Gln Pro Ile Asn Leu Ile Phe Arg Phe
1               5                  10                  15

Leu Gln Ser Lys Ala Arg Ile Gln Ile Trp
            20                  25
```

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Lys Val Gln Lys Val Met Val Gln Pro Ile Asn Leu Ile Phe Arg Tyr
1               5                  10                  15

Leu Gln Asn Arg Ser Arg Ile Gln Val Trp
            20                  25
```

(2) INFORMATION FOR SEQ ID NO:7:

(i) SEQUENCE CHARACTERISTICS:

(A) LENGTH: 7 bases
      (B) TYPE: nucleic acid
      (C) STRANDEDNESS: single
      (D) TOPOLOGY: unknown (ii) MOLECULE TYPE: RNA (xi) SEQUENCE DESCRIPTION: SEQ ID NO:7:

CNACNNU                                                                                 7

(2) INFORMATION FOR SEQ ID NO:8:

(i) SEQUENCE CHARACTERISTICS:
      (A) LENGTH: 25 bases
      (B) TYPE: nucleic acid
      (C) STRANDEDNESS: single
      (D) TOPOLOGY: unknown (ii) MOLECULE TYPE: RNA (xi) SEQUENCE DESCRIPTION: SEQ ID NO:8:

CUAUUUGGCU CAACUCUCCG AGUUA                                                            25

(2) INFORMATION FOR SEQ ID NO:9:

(i) SEQUENCE CHARACTERISTICS:
      (A) LENGTH: 25 bases
      (B) TYPE: nucleic acid
      (C) STRANDEDNESS: single
      (D) TOPOLOGY: unknown (ii) MOLECULE TYPE: RNA (xi) SEQUENCE DESCRIPTION: SEQ ID NO:9:

AGUUAGCCAA CCACAAUAGA GUGGA                                                            25

(2) INFORMATION FOR SEQ ID NO:10:

(i) SEQUENCE CHARACTERISTICS:
      (A) LENGTH: 25 bases
      (B) TYPE: nucleic acid
      (C) STRANDEDNESS: single
      (D) TOPOLOGY: unknown (ii) MOLECULE TYPE: RNA (xi) SEQUENCE DESCRIPTION: SEQ ID NO:10:

UCAAUGAUCA CUACUUUCUU AAACC                                                            25

(2) INFORMATION FOR SEQ ID NO:11:

(i) SEQUENCE CHARACTERISTICS:
      (A) LENGTH: 25 bases
      (B) TYPE: nucleic acid
      (C) STRANDEDNESS: single
      (D) TOPOLOGY: unknown (ii) MOLECULE TYPE: RNA (xi) SEQUENCE DESCRIPTION: SEQ ID NO:11:

UGUUGUCUUA CUACAAUACC GCUCG                                                            25

(2) INFORMATION FOR SEQ ID NO:12:

(i) SEQUENCE CHARACTERISTICS:
      (A) LENGTH: 25 bases
      (B) TYPE: nucleic acid
      (C) STRANDEDNESS: single
      (D) TOPOLOGY: unknown -continued

```
    (ii) MOLECULE TYPE: RNA (xi) SEQUENCE DESCRIPTION: SEQ ID NO:12:

UACUAGGUAG CCACAUUAUA GCCGU                                              25

(2) INFORMATION FOR SEQ ID NO:13:

(i) SEQUENCE CHARACTERISTICS:
        (A) LENGTH: 25 bases
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:13:

CGCUCAUGUU CGACGCUAUC GAAAA                                              25

(2) INFORMATION FOR SEQ ID NO:14:

(i) SEQUENCE CHARACTERISTICS:
        (A) LENGTH: 25 bases
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:14:

CGCUCAUGUU CGACGCUAUU AUGGA                                              25
```

NUCLEAR RESTORER GENES FOR HYBRID SEED PRODUCTION

This application is a continuation-in-part of copending U.S. patent application Ser. No. 08/346,611, which was filed on Nov. 29, 1994 and which issued as U.S. Pat. No. 5,648,242, on Nov. 4, 1997.

GOVERNMENT SUPPORT

This invention was made with government support under Grant Nos. GAM9001136, AMD9201761, and 9400901, all awarded by the United States Department of Agriculture. Therefore, the United States Government may have certain rights in this invention.

TECHNICAL FIELD OF THE INVENTION

The present invention relates to the production of hybrid seed. More specifically, the present invention relates to the use of certain cloned nuclear restorer genes, which are involved in the reversion of cytoplasmic male sterility, in the production of hybrid seed and other applications.

BACKGROUND OF THE INVENTION

In plants, the best first filial ($F_1$) hybrids have a substantial yield advantage over the best open-pollinated varieties or inbred lines. This yield advantage of a hybrid over its parents is termed "heterosis." The observed degree of heterosis varies among species; however, as a general rule, it is high among cross-pollinated species, such as maize and sunflower, and typically lower among self-pollinated species, such as soybean and wheat.

In this regard, from at least about the 1940's, hybrid varieties of maize (a/k/a corn) largely supplanted open-pollinated varieties because startling improvements in yield, along with other agronomic traits, were realized when hybrid varieties were used. Indeed, the manufacture and sale of hybrid seed are the basis of a significant agricultural industry.

To obtain $F_1$ hybrid seed, it is necessary to cross two inbred parents. Although it is possible to do this via controlled pollinations (i.e., fertilizations) flower by flower, such an approach is labor-intensive and, thus, very expensive. Only high-value crops, such as ornamental flowers and the like, could absorb such production costs.

In maize, an intermediate course historically has been taken. Two maize parents have been grown in isolation from other potential maize parents, i.e., sources of pollen. One parent was detasseled (emasculated) and served as the "female" parent, whereas the other parent was allowed to produce pollen and fertilize the female parent by cross-pollination, thereby serving as a "male" parent. Which maize parent was chosen to be the female and which maize parent was chosen to be the male were frequently based on commercially significant reasons. For example, it was preferred to use maize with ample seed production as a female parent and maize with ample pollen production as a male parent. Hybrid seed was then harvested from the female parent.

The use of detasseling to emasculate a plant to provide a female parent for hybrid seed production continued until the discovery of cytoplasmic male sterility ("CMS"). CMS obviated the need to detassel because the products of genes involved in CMS caused ill-formed anthers that did not produce viable pollen. The causative factors of CMS have been shown to reside in the plant cell's cytoplasm (see Laughnan et al., *Ann. Rev. Genet.*, 17, 27–48 (1983)). Such factors have been determined to be associated with mitochondria, which are maternally inherited. Accordingly, a cytoplasmic male-sterile line, which is incapable of cross- or self-pollination, can be used as a female parent. By crossing such a female parent with a pollen-producing line, fertile hybrid seed can be generated without detasseling the female plants.

An inbred line of maize can be converted into a CMS line by crossing it (as male) to a known cytoplasmic male-sterile line and then backcrossing it (as female) to the original inbred line. Given that the CMS-converted line is male-sterile, it must be maintained by crossing by the original inbred line (a "maintainer"). Hybrid seed is produced by growing the CMS-converted inbred line and a second inbred line in isolation, without detasseling.

Cytoplasmic male-sterile maize can be restored to fertility in a succeeding generation by a nuclear restorer gene. For example, if a CMS-converted line is grown in isolation with a second inbred line carrying a nuclear restorer gene, then the $F_1$ will be male-fertile and potentially economically valuable.

There are three types of male-sterile cytoplasms in maize (*Zea mays* L. ): S (USDA), C (Charrua), and T (Texas). These three male-sterile cytoplasms can be distinguished by the ability of different nuclear (restorer) genes to restore fertility to the plants with these different cytoplasms (see Laughnan et al. (1983), supra), by mitochondrial DNA restriction endonuclease profiles (see Pring et al., *Genetics*, 89, 121–136 (1978)), and by $^{35}$S-methionine-labeled polypeptides translated in isolated mitochondria (see Forde et al., *PNAS USA*, 75, 3841–3845 (1978)).

In contrast to the male-sterile cytoplasms, the normal (N), male-fertile cytoplasm yields fertile plants in either the presence or absence of all known nuclear backgrounds, whereas the male-sterile C, S, and T cytoplasms only produce fertile plants in nuclear backgrounds carrying the appropriate restorer genes. These nuclearly encoded, fertility-restorer genes compensate for cytoplasmic dysfunction(s) that are phenotypically expressed during microsporogenesis and/or microgametogenesis. Plants carrying S or C cytoplasm are restored to fertility by a single dominant allele of the rf3 or rf4 locus, respectively. Preliminary evidence suggests that the rf3 locus is flanked by whp and bn117.14 on chromosome 2L (Kamps et al., *Maize Genet. Coop. Newsl.*, 66, 45 (1992)). The rf4 locus maps to chromosome 8, approximately 2 cM from the RFLP ("restriction fragment length polymorphism") marker NP1114A (Sisco, *Crop Sci.*, 31, 1263–1266 (1991)). In contrast to S and C cytoplasms, plants with T cytoplasm are restored to fertility by the dominant alleles of two loci, rf1 and rf2 (Laughnan et al. (1983), supra; and Levings et al., *Plant Cell*, 5, 1285–1290 (1983)), which are located on separate chromosomes. The rf1 locus is flanked by umc97 and umc92 on chromosome 3, and the rf2 locus is flanked by the umc153 and sus1 on chromosome 9 (Wise et al., *Theor. Appl. Genet.*, 88, 785–795 (1994)).

T cytoplasm is restored to fertility at the sporophytic level; the genetic constitution of the diploid, sporophytic anther tissue, rather than that of the haploid, gametophytic pollen grain, determines pollen development. Therefore, a T-cytoplasmic plant, which is heterozygous for both restorer gene loci (Rf1/rf1, Rf2/rf2), will produce all normal pollen even though only one-fourth of the pollen grains carry both Rf1 and Rf2 (Laughnan et al. (1983), supra). In contrast, S-cytoplasm is restored to fertility at the gametophytic level, and, therefore, an S-cytoplasmic plant, which is heterozygous for rf3 (Rf3/rf3), will produce half normal pollen because only one-half of the pollen grains carry Rf3 (Laughnan et al. (1983), supra; and Schardl et al., *Cell*, 43, 361–368 (1985)).

CMS also occurs in other species of plants. Examples of other species of plants include petunia (Nivison et al., *Plant Cell*, 1, 1121–1130 (1989)), the common bean (Janska et al., *Genetics*, 135, 869–879 (1993)), *Brassica napus* (Singh et al., *Plant Cell*, 3, 1349–1362 (1991)), sunflower (Laver et al., *The Plant Journal*, 1, 185–193 (1991)), sorghum (Bailey-Serres et al., *Theor. Appl. Genet.*, 73, 252–260 (1986)), and oats (Mann et al., *Theor. Appl. Genet.*, 78, 293–297 (1989)). Like S-cytoplasmic maize, cytoplasmic male sterility in petunia, beans, and Brassica can be restored to fertility by single dominant nuclear genes.

Most of the research on CMS has focused on the characterization of novel open reading frames present in the mitochondrial genomes of male-sterile cytoplasms. Such research has revealed that, although each open reading frame is unique, all appear to have large hydrophobic domains (Dewey et al., *PNAS USA*, 84, 5374–5378 (1987)).

In T-cytoplasmic maize, CMS is associated with the unique mitochondrial gene T-urf13 (Wise et al., *PNAS USA*, 84, 2858–286 (1987a)). Toxin sensitivity traits are also associated with this gene (Huang et al., *EMBO*, 9, 339–247 (1990)). T-urf13 encodes a 13 kDa mitochondrial polypeptide (URF13) (Wise et al., *Plant Mol. Biol.*, 9, 121–126 (1987b)), which is located in the mitochondrial membrane (Dewey et al. (1987), supra) and appears to span the mitochondrial membrane in oligomeric form (Korth et al., *PNAS USA*, 88, 10865–10869 (1991)). URF13 is not synthesized by deletion mutants (Dixon et al., *Theor. Appl. Genet.*, 63, 75–80 (1982)), is truncated in the T4 frameshift mutant (Wise et al. (1987b), supra), and binds to fungal pathotoxins (Braun et al., *Plant Cell*, 2, 153–161 (1990)).

The abundance of URF13 is reduced by approximately 80% in plants carrying Rf1 and Rf2 (Dewey et al. (1987), supra). Also, there is an additional 1.6 kb T-urf13-specific transcript in such plants (Kennell et al., *Mol. Gen. Genet.*, 210, 399–406 (1987)). The alteration of T-urf13 transcript accumulation and the concurrent reduction of URF13 appear to require the action of Rf1 only (Dewey et al. (1987), supra); however, other modifiers also appear to have an effect on T-urf13 transcript accumulation, depending on the nuclear background (Kennell et al. (1987), supra). Little is known about Rf2 except that, in addition to Rf1, it is essential for pollen restoration.

T cytoplasm was used predominantly in the late 1960's because of its reliability. The other male-sterile cytoplasms of maize, namely C and S, tended to "break down" in the field, i.e., self-pollination or incomplete fertility restoration occurred. Thus, approximately 85% of the hybrid maize seed in the U.S. was T-cytoplasm until the epidemic of southern corn leaf blight, which occurred in 1970 (Pring et al., *Ann. Rev. Phytopathol.*, 27, 483–502 (1989)).

After the 1970 epidemic, it was determined that T-cytoplasmic maize is highly sensitive to the host-selective toxin (T toxin) produced by race T of the fungus *Cochliobolus heterostrophus* Drechsler (asexual stage *Bipolaris maydis* Nisikado and Miyake), which is the causal organism of southern corn leaf blight (Comstock et al., *Phytopathology*, 63, 1357–1361 (1973)). T-cytoplasmic maize was also found to be highly sensitive to the host-selective toxin (Pm toxin) produced by another fungus, namely *Phyllosticta maydis*, Arny and Nelson, which causes yellow leaf blight (Yoder, *Phytopathology*, 63, 1361–1366 (1973)).

In view of the above, the major seed producers in the U.S. now use various combinations of male-sterile cytoplasms (including T). The use of various combinations of male-sterile cytoplasms enables a farmer to sow his fields with seeds of, for example, T, C, S, and N cytoplasms, wherein only those plants of N cytoplasm might entail detasseling.

A focus of research since the 1970's has been to develop alternative genetic approaches to emasculating plants for the purpose of hybrid seed production. This effort, in part, reflects a desire among farmers to maintain some level of genetic heterogeneity for any given crop. One approach (Marc Albertsen, Pioneer Hi-Bred International, Inc.) involves the use of nuclear male-sterile genes. This particular approach, which is predicated, at least in part, on earlier analogous work with Arabidopsis (see Aarts et al., *Nature*, 363, 715–717 (1993)), specifically uses a cloned nuclear male-sterile gene from maize, although there are a number of such genes in a given plant species, including maize (Albertson et al., *Can. J. Genet. Cytol.*, 23, 195–208 (1981)). An inbred line of maize, for example, which is homozygous for a mutant allele of a nuclear male-sterile (ms) gene, is genetically engineered to carry a construct comprising an inducible promotor, which, upon induction, allows expression of a wild-type ms gene. The inbred line is maintained in isolation, where it is sprayed with the inducer and allowed to self- and sib-pollinate. Hybrid seed is produced by growing the inbred line with a second inbred line, which carries a wild-type allele of the ms gene, in isolation and in the absence of inducer. Accordingly, the $F_1$ is heterozygous and, therefore, fertile. This approach is disadvantageous, however, in that it requires maintenance of the male-sterile line and the use of an inducer.

Another approach involves the use of a construct comprising an RNase gene operably linked to a tapetum-specific promotor (Leemans et al., Plant Genetic Systems; and Leemans et al., *Nature*, 347, 737–741 (1990)). The RNase is active only in the anthers, where it kills the tapetum, i.e., a structure that normally nourishes pollen. Introduction of this construct, via transformation or backcrossing, into an inbred line results in heterozygous dominant male sterility. When the heterozygous dominant male-sterile line is crossed by a N-cytoplasmic line, the progeny segregate for is and N (i.e., normal). Tight linkage of an herbicide resistance gene to the RNase gene enables elimination of fertile segregants. In practice, the male-sterile line is crossed by a normal progenitor line. The resulting segregating progeny are grown in isolation with a second inbred line. The rows that carry the first inbred line are sprayed with an herbicide. The male-fertile progeny die, leaving only the male-sterile inbred plants from which hybrid seed can be harvested. This approach is disadvantageous in that it requires the use of an herbicide to eliminate fertile plants, the presence of which reduce overall yield.

In view of the above, it is evident that there remains a need for an efficient and economical method of producing hybrid seed in high yield with a low risk of disease. Accordingly, it is an object of the present invention to provide new materials and methods that will enable one to produce hybrid seed from new and existing cytoplasmic male-sterile lines without the disadvantages attendant materials and methods currently available in the art. It is another object of the present invention to provide a method of producing a variant of a cytoplasmic male-sterile plant. It is yet another object of the present invention to provide a method of suppressing cytoplasmic male sterility in the progeny of a cytoplasmic male-sterile plant. These and other objects and advantages of the present invention, as well as additional inventive features, will be apparent from the description of the invention provided herein.

SUMMARY OF THE INVENTION

The present invention provides an enriched or substantially isolated nucleic acid comprising a nucleotide sequence that encodes a nuclear male fertility restorer gene. Preferably, the nucleotide sequence hybridizes under moderately stringent conditions to SEQ ID NO: 4 and restores male fertility to a cytoplasmic male-sterile plant. Vectors, organisms, viruses, seeds, plant cells, and plants comprising such a nucleic acid, in particular a nucleic acid comprising the preferred nucleotide sequence, also are provided.

Also provided is a method of producing hybrid seed, which method comprises the steps of: (a) obtaining a nucleic acid comprising a nucleotide sequence, which hybridizes at least under moderately stringent conditions to SEQ ID NO: 4 and restores male fertility to a cytoplasmic male-sterile plant; (b) introducing the nucleic acid of (a) into a plant cell; (c), generating a plant from the plant cell of (b), which comprises and expresses the nucleic acid of (a); (d) pollinating a cytoplasmic male-sterile plant by the plant. of (c); and (e) obtaining a seed, which generates a fertile plant, from the cytoplasmic male-sterile plant of (d)

In another embodiment of a method of producing hybrid seed provided by the present invention, a first plant, which is homozygous for a leaky mutant allele of Rf1 or Rf2, and a second plant, which comprises a defective cytoplasm as defined herein, are generated. Then, the second plant is pollinated by the first plant, and a seed, which generates a fertile plant, is obtained from the second plant. Alternatively, a seed is obtained from the second plant and is grown into a sterile plant, the male-sterile progeny of which are then backcrossed by a plant like the first plant until a plant, which is homozygous for the leaky mutant allele of Rf1 or Rf2, is obtained. Accordingly, a variant of a cytoplasmic male-sterile plant is provided.

In yet another embodiment of the present invention, a method of suppressing cytoplasmic male sterility in the progeny of a cytoplasmic male-sterile plant is provided. In this method, an RNA-processing encoding region of a gene, such as a snRNP- or U2AF-1-encoding region, is coupled to a mitochondrial targeting sequence and introduced into a vector. The snRNP or U2AF-1 can be engineered to recognize a specific nucleotide sequence, such as an RNA or protein binding site, e.g., 5'-CNACNNU-3' (SEQ ID NO: 7 and FIG. 1 (SEQ ID NOS: 8–14)), in a cytoplasmic male sterility sequence. The vector is then introduced into a plant cell, and a first plant, which comprises and expresses an RNA-processing encoding region (e.g., snRNP or U2AF-1), is generated. A second plant, which is cytoplasmic male-sterile and which comprises a cytoplasmic male sterility sequence comprising a nucleotide sequence recognized by the RNA-processing encoding region (snRNP/U2AF-1), is then pollinated by the first plant. The RNA-processing (e.g., snRNP/U2AF-1) complex then cleaves the cytoplasmic male sterility sequence at the specific nucleotide sequence recognized by the RNA-processing encoding region and expression of the cytoplasmic male sterility sequence is suppressed in the progeny of the second, cytoplasmic male-sterile plant. Accordingly, this method provides a means of suppressing cytoplasmic male sterility.

BRIEF DESCRIPTION OF DRAWINGS

FIG. 1 is a comparison of RNA processing sites between maize, sorghum, archaea and rice.

FIG. 4 is a comparison of the predicted amino acid sequence of Rf1 cDNA p6140-1 nts 1468–1545 with the amino acid sequence of human snRNP E.

DETAILED DESCRIPTION OF THE PREFERRED EMBODIMENTS

Figure 2:
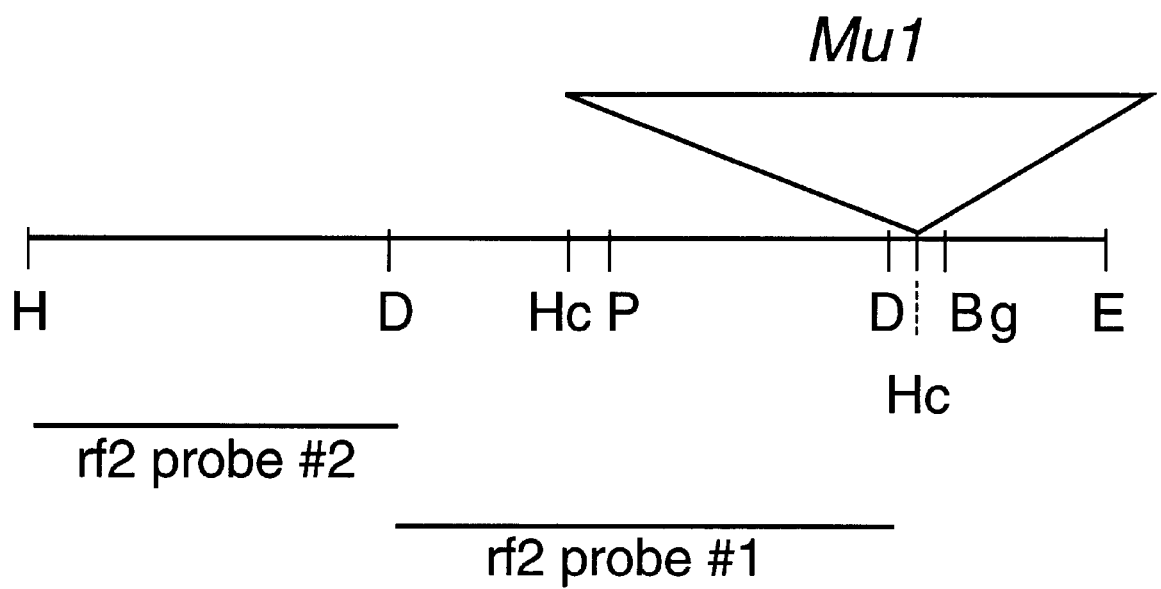
FIG. 2 is a restriction endonuclease map of pRf2.

The present invention provides certain genetic sequences relating to restoration of male fertility in cytoplasmic male-sterile plants, and further provides methods for the use of such sequences in the production of hybrid seed and the generation of new variants of cytoplasmic male-sterile plants.

In particular, the present invention provides an enriched or substantially isolated nucleic acid comprising a nucleotide sequence comprising a plant-derived nuclear restorer gene, or a portion thereof, the action of which is to restore male fertility to a cytoplasmic male-sterile plant. As used herein, cytoplasmic male sterility is considered to be the direct result of one or more factors, which can be the product of one or more genes. A nuclear restorer gene product can be a polypeptide or an RNA molecule. The nuclear restorer gene product is involved in restoring male fertility typically by action on mitochondrial or chloroplastic functions.

The term "nucleic acid" refers to a polymer of DNA or RNA, i.e., a polynucleotide, which can be single- or double-stranded, and can optionally contain synthetic, nonnatural, or altered nucleotides. Any combination of such nucleotides can be incorporated into DNA or RNA polymers. The nucleic acid is "enriched" in that the concentration of the material is at least about 2, 5, 10, 100, or 1,000 times its natural concentration, for example, advantageously about 0.01% by weight, preferably at least about 0.1% by weight. Enriched preparations of about 0.5%, 1%, 5%, 10%, and 20% or more by weight are also contemplated. A nucleic acid is "isolated" in that the material has been removed from its original environment, e.g., the genome of a plant, presuming that it is naturally occurring. Thus, describing the nucleic acid of the present invention as "substantially isolated" reflects the increase in concentration of the nucleic acid of interest with respect to other nucleic acids, as when, for example, the nucleic acid of interest is taken from a plant (which, in the case of maize, has a complement of three million kb) and is placed or cloned into a bacteriophage (which, in the case of lambda ("λ") has a complement of 50 kb), resulting in a 60,000-fold increase in concentration of the nucleic acid of the present invention with respect to the total amount of DNA in the bacteriophage into which it is placed. It is also advantageous that the nucleic acids be in purified form, or substantially purified form, wherein "purified" does not mean absolute purity but, rather, relative purity, wherein, for example, the nucleic acids of the present invention are isolated in a laboratory vessel in a mixture of other nucleic acids, such as portions of a vector or other molecules associated with genetic engineering.

Preferably, the enriched or substantially isolated nucleic acid hybridizes under at least moderately stringent hybridization conditions to a second nucleic acid comprising a nucleotide sequence specific to a plant-derived restorer gene (Rf), or a substantial portion thereof; more preferably, the nucleic acid hybridizes under the aforementioned conditions to a second nucleic acid comprising a nucleotide sequence specific to the Rf1 or Rf2 gene of maize, or a substantial portion thereof.

Stringency of hybridization is a term of art that refers to the conditions used for a hybridization reaction, wherein complementary single strands of nucleic acid join to one another to form double-stranded nucleic acid with some degree of mismatch, the degree of which is a function of the stringency of the hybridization conditions used. In particular, the stringency will depend upon the size and composition of the strands of nucleic acid that are caused to react, the degree of mismatching allowed, the desired crossreactivity, and the like. The degree of stringency can be affected by the ionic conditions employed and temperature, among others, as is well-known in the art. Sambrook et al., *Molecular Cloning: A Laboratory Manual* (2d ed., 1989).

The specified stringency of hybridization, in part, defines the nucleic acid of the present invention. Accordingly, the hybridization conditions are designed suitably to be at least moderately stringent or stringent. In the former case, suitable conditions of salt, temperature, reaction mixture, and size of nucleic acid reactants are set in accordance with conventional knowledge to provide from about 45% to about 70% mismatch of the sequence of nucleotides of the nuclieic acids. Preferably, moderately stringent hybridization conditions are set to provide from about 55% to about 75% mismatch; and more preferably, such conditions are set to provide from about 60% to about 70% mismatch. In the latter case, suitable conditions for hybridization are set in accordance with conventional knowledge to provide from about 10% to about 40% mismatch. Preferably, stringent hybridization conditions are set to provide from about 20% to about 40% mismatch; and more preferably, such conditions are set to provide from about 30% to about 40% mismatch. By mismatch, it is meant the decree to which noncomplementary base pairs are found opposite one another in an otherwise duplex nucleic acid, thereby forming bubble structures and causing the welting temperature of the duplex to be lower as compared to a 100% matched duplex of the same length and base composition.

The present invention is also directed to a nucleic acid as described herein above comprising regulatory sequences. Preferably, such regulatory sequences are specific for plants, fungi, or bacteria. More preferably, such regulatory sequences are specific for one or more plants, such as one of agronomic or ornamental value. In this context, developmental or tissue-specific regulatory sequences, for example, can be used. Such regulatory DNA sequences are known to those of ordinary skill in the art.

The nucleic acid of the present invention can be isolated from any suitable, sexually-reproducing plant, which can be monocotyledonous or dicotyledonous, as long as the plant comprises an Rf gene as described herein. Preferred plants include maize, wheat, barley, rice, common bean, oats, rye, soybean, rapeseed, canola, cotton, safflower, peanut, palm, sorghum, sunflower, beet, tomato, cucumber, petunia and other ornamental flowers. The more preferred plant from which the Rf gene is derived is maize.

The Rf2 nuclear restorer gene was isolated from a cDNA library derived from the mRNA present in tassel tissue. Construction of the cDNA library and the appropriate harvesting of the tassel tissue was accomplished using conventional knowledge and techniques, using bacteriophage lambda as host for the cDNA library.

The isolated Rf2 cDNA sequence has a high degree of homology to aldehyde dehydrogenase from various sources, including cows and rats. Aldehyde dehydrogenase is a "housekeeping" enzyme, which functions in the mitochondrion or cytosol. In the liver of a mammal, for example, it is also known to play a role in detoxification.

The Rf1 nuclear restorer gene was isolated from a cDNA library derived from the mRNA present in seedlings. Construction of the cDNA library and the appropriate harvesting of seedlings was accomplished using conventional knowledge and techniques, using bacteriophage lambda as host for the cDNA library.

The isolated Rf1 cDNA sequence has a high degree of homology to small nuclear ribonucleoprotein E (snRNP E), which is involved in RNA processing. In fact, 26 amino acids of the predicted amino acid sequence of nts 1468–1545 of the Rf1 cDNA p6140-1 are 96% homologous and 69% identical with mammalian snRNP E as shown in FIG. 4.

Accordingly, the present invention provides a nucleic acid comprising a nucleotide sequence, which hybridizes under at least moderately stringent conditions, to SEQ ID NOS: 1, 3 or 4, or a sequence complementary thereto. SEQ ID NO: 1 and SEQ ID NO: 3 comprise the same nucleotides; however, SEQ ID NO: 1 comprises two additional nucleotides designated N in the Sequence Listing. A preferred enriched or substantially isolated nucleic acid comprises a nucleotide sequence, which hybridizes to SEQ ID NO: 1, 3 or 4 only under stringent hybridization conditions. A more preferred enriched or substantially isolated nucleic acid comprises a nucleotide sequence selected from the group consisting of SEQ ID NO: 1, SEQ ID NO: 3, SEQ ID NO: 4, a sequence complementary to any one of SEQ ID NOS: 1, 3 and 4, a sequence substantially equivalent to any one of SEQ ID NOS: 1, 3 and 4, and a sequence substantially equivalent to a sequence complementary to any one of SEQ ID NOS: 1, 3 and 4.

SEQ ID NO: 1 is a partial sequence (402 bases sequenced out of a total of about 1200 bases;) of the cDNA derived from the maize Rf2 gene, the identification and isolation of which are described in Examples 1 and 2. SEQ ID NO: 1 does not appear to be a full-length cDNA (i.e., including the complete complement of the Rf2 mRNA) because, as compared to the evidently homologous aldehyde dehydrogenase gene sequences disclosed in Example 4, approximately 500 bp of the Rf2 message is missing. Nevertheless, one of ordinary skill in the art certainly recognizes that either one of SEQ ID NO: 1 and SEQ ID NO: 3 provides sufficient Rf2 sequence information to provide probes for the identification and cloning of any Rf2 gene or to any gene that is substantially homologous to Rf2 in sequence, such that the Rf2 probe hybridizes under moderately stringent to stringent hybridization conditions, as discussed herein above. Accordingly, the present invention also provides Rf2-specific probes.

SEQ ID NO: 4 is a sequence of a total of about 2473 bases, including poly A, of the cDNA derived from the maize Rf1 gene, the identification and isolation of which are described in Examples 6–8. Accordingly, the present invention also provides Rf1-specific probes.

A "substantially equivalent" sequence is a sequence that, with respect to SEQ ID NO: 1, for example, varies from the SEQ ID NO: 1 sequence by one or more substitutions, deletions, or additions, the effect of which does not result in an undesirable functional dissimilarity between the two sequences. Thus, conventionally known "neutral mutations," which have no impact on the resultant amino acid sequence, are fully included in this definition. Also included in the definition are conventionally known "conservative mutations," which does change some of the resultant amino acids for those of approximately equivalent size, shape and charge characteristics, such as, for example, an isoleucine or glycine for a leucine, but such exchange has little or no deleterious impact on the functioning of the resultant protein with respect to the progenitor protein. In other words, the polypeptide that results from the substantially equivalent sequence has the activity characteristic of the Rf2 gene product, for example. A difference in sequence at the amino acid level will be understood to include amino acid differences that range from a single amino acid substitution, deletion, or insertion to a number of amino acid substitutions, deletions, and/or insertions, wherein the resulting polypeptide is still recognizable as related to the Rf2 protein, for example, as well as those amino acid sequence differences, which result in a larger polypeptide, such as a precursor protein, a complete mature protein, or a truncated protein. Accordingly, even non-conservative exchanges of amino acids with respect to the progenitor protein can be included in the embodiment of the present invention so long as the Rf gene product activity remains substantially unchanged.

A nucleic acid can be identified for enrichment or substantial isolation by hybridization to any subfragment of SEQ ID NOS: 1, 3 or 4 of at least 20 nucleotides under stringent hybridization conditions as described in Sambrook et al., *Molecular Cloning: A Laboratory Manual* (2d ed., 1989). Accordingly, this invention encompasses the entire sequence of the Rf1 and Rf2 genes and fragments thereof, which have been generated by any suitable technique, such as by restriction enzyme digestion of chromosomal or plasmid DNA, by PCR, or by synthesis, and which can be either DNA or RNA.

In addition to the methods recited in the examples for the identification and isolation of nuclear restorer genes and related nucleic acids, other methods also can be used, such as, inter alia, chromosome walking and heterologous probe selection.

Chromosome walking is a particularly useful technology that can facilitate the molecular isolation of any mapped gene (Bender et al., *J. Mol. Biol.*, 168, 17–338 (1983)) and has been found to be particularly useful with plants that have a relatively small genoine size, such as that of Arabidopsis. This technique is useful, of course, in species of larger genome size as well, such as maize.

A chromosome walk is initiated by identifying from a library of large DNA fragments the specific fragment(s) that contain sequences homologous to a restriction fragment length polymorphism (RFLP) marker or some other marker that is closely linked to the target gene. Typically, the library of DNA fragments is maintained as yeast artificial chromosomes, i.e., YACs (Burke et al., *Science*, 236, 806–811 (1987)), although cosmids, P1 phage or λ phage have been used. Single copy sequences from the termini of YACs that contain sequences homologous to a starting RFLP are then used as hybridization probes to isolate overlapping DNA fragments. This process is repeated until the entire chromosomal region, from the starting RFLP marker to beyond the target gene, has been cloned as a contiguous segment (a "contig"). Typically, the contig is oriented by mapping DNA sequences from the growing contig to the genetic/RFLP map. Similarly, the endpoint of the walk is established by demonstrating that the contig contains DNA sequences from both sides of the target gene. For both of these operations, DNA sequences from the contig must be genetically mapped. The efficiency of this mapping can be greatly increased by selecting a population of plants that have a high probability of carrying recombination breakpoints in the region defined by the contig. Such a mapping population is established by selecting plants that carry a recombination breakpoint between two visible genetic markers that flank the interval to be walked. The precision of the mapping increases proportionally with the number of genetic recombinants. The greater the precision of this mapping, the smaller the uncertainty associated with the positioning of the target gene on the contig. Once the target gene has been localized in the contig to as small an interval as the mapping population permits, the target gene is identified from the interval via its ability to complement genetically the mutant phenotype. The ability of a sequence to complement the mutant phenotype is assayed by transforming plants homozygous for a mutant allele of the target gene. Alternatively, comparisons between wild-type And mutant sequences also can identify the target gene from the interval.

Other technologies for gene isolation in Arabidopsis and other plants include genomic subtraction, and transposon and T-DNA tagging. Genomic subtraction requires the availability of strains having deletions of the target gene (Strauss and Ausubel, *PNAS USP*, 87, 1889–1893 (1990); and Sun et al., *Plant Cell*, 4, 119–128 (1992)); however, such deletions are not available for rf2, for example. A transposon tagging system in Arabidopsis has recently become available. The success in tagging and cloning a petunia gene using a heterologous maize transposon (Chuck et al., *Plant Cell*, 5, 371–378 (1993)) provided the direction to extend this technique to Arabidopsis, and further demonstrates that this technique is amenable to tagging virtually any plant with heterologous (Dean et al., *Plant J.*, 2, 69–81 (1992); Grevelding et al., *PNAS USA*, 89, 6085–6089 (1992); Swinburne et al., *Plant Cell*, 4, 583–595 (1992); and Fedoroff and Smith, *Plant J.*, 3, 273–289 (1993)) and/or endogenous (Tsay et al., *Science*, 260, 342–344 (1993)) transposons. T-DNA tagging has been realized (Feldmann, *Plant J.*, 1, 71–82 (1991)) and is in wide use (e.g., Feldmann et al., *Science*, 243, 1351–1354 (1989); Herman et al., *Plant Cell*, 11, 1051–1055 (1989); Konz et al., *EMBO J.*, 9, 1337–1346 (1989); and Kieber et al., *Cell*, 72, 427–441 (1993)). Additionally, having isolated at least two nuclear restorer genes, the nucleic acid thereof can be used whole or in parts (by sub-cloning fragments thereof) as a probe in heterologous systems. Preferably, such a technique requires that the stringency of the selective hybridization procedure be lowered, and then slowly raised, as is well known in the art.

Although T-DNA tagging, chromosome walking or heterologous probe selection can identify a DNA fragment that putatively contains the gene of interest, in each instance these DNA fragments must be confirmed by genetic complementation or some other means, which is fully disclosed in the examples. Although the methods of identification of a particular gene sequence have been described largely herein with reference to maize and Arabidopsis only, it is abundantly clear to one of ordinary skill that such methods can be adapted for gene identification in other species, particularly in the context of the present invention. Accordingly, the identification of the Rf genes, and cloning and use thereof, is enabled hereby for any of the aforementioned sexual-reproducing plants, as well as other plants that have mitochondrial deficiency-derived phenotypes in need of amelioration or correction, in particular those mitochondrial deficiencies amenable to amelioration or correction by one or more of the nucleic acids described herein.

The nucleic acids of the present invention can be cloned in any suitable vector, and the resultant vector can be used to transform or transfect any suitable host. *E. coli*, in particular *E. coli* TB-1, TG-2, DH5α, XL1-Blue MRF' (Stratagene), SA2821 or Y1090, is a preferred host. A more preferred host is XL-Blue MRF' or TG-2. Suitable vectors include those designed for propagation and expansion or for expression or both. Constructs of vectors can be prepared, either circular or linear, to contain the entire nucleotide sequence of an Rf gene or a portion thereof ligated to a replication system functional in a microorganismic host, whether prokaryotic or eukaryotic. Suitable hosts include *E. coli, B. subtilis, P. aerugenosa, S. cerevisiae*, and *N. crassa*. Replication systems can be derived from ColE1, 2 mμ plasmid, lambda, SV40, bovine papilloma virus, or the like. In addition to the replication system and the inserted DNA, the construct usually will include one or more markers, which allow for selection of transformed or transfected hosts. Markers may include biocidie resistance, e.g., resistance to antibiotics, heavy metals, etc., complementation in an auxotrophic host to provide prototrophy, and the like. A preferred cloning vector is selected from the group consisting of pUC18, pET11d, EMBL4, NM1149, pLZO3 and Lambda ZapII (Stratagene). Of course, it is well-appreciated in the art that nucleic acids can be cloned in suitable bacteriophage vectors, such as, for example λGT10.

The present invention provides expression vectors for the expression of such polypeptides. A preferred expression vector is one that comprises a nucleic acid comprising, as an insert, a nucleotide sequence of a nuclear restorer gene, preferably one that is enriched or substantially isolated from one of the aforementioned sexually reproducing plants. A more preferred expression vector comprises a nucleic acid comprising a nucleotide sequence, which hybridizes at least under moderately stringent conditions to a sequence selected from the group consisting of SEQ ID NO: 1, SEQ ID NO: 3, SEQ ID NO: 4, a sequence complementary to any one of SEQ ID NOS: 1, 3 and 4, a sequence substantially equivalent to any one of SEQ ID NOS: 1, 3 and 4, and a sequence substantially equivalent to a sequence complementary to any one of SEQ ID NOS: 1, 3 and 4.

One skilled in the art will appreciate that any one of a number of expression vectors can be utilized in the context of the present invention with some degree of success, including, but not limited to, the following: pGEX2T, pATH11, pNH8A (Stratagene, Inc., La Jolla, Calif., pGL2 (Promega, Madison, Wis.), pEX2 (Boehringer Mannheim Biochemicals, Indianapolis, Ind.), and pMOSELlox (Amersham Corporation, Arlington Heights, Ill.). Additionally, vectors known in the art for expression of exogenous DNA in plant cells can be used.

Care should be taken to choose a vector that does not result in cytotoxic expression of any amino acid sequence encoded in the insert of the vector. For expression in microorganisms, the expression vector can differ from the cloning vector in having transcriptional and translational initiation and termination regulatory signal sequences and can or cannot include a replication system that is functional in the expression host. The coding sequence is inserted between the initiation and termination regulatory signals so as to be under their regulatory control. Expression vectors can also include the use of regulatable promoters, e.g., temperature-sensitive or inducible, such as by chemicals, or genes that allow for integration and amplification of the vector and insert DNA, such as tk, dhfr, metallothionein, and the like. Such controls, if incorporated into a plant, could allow for the efficient and economic production of hybrid seeds, for example, by promoting expression of the restorer gene function upon the advent of a triggering level of an inducer.

The vector can be used to express a dsDNA sequence, either isolated and cloned or synthesized, to obtain a functional RNA molecule, a precursor protein, which is subject to further manipulation by cleavage, a complete mature protein, or a fragment thereof by introducing the expression vector into an appropriate host, where the regulatory signals are functional in the host. The expression host is grown in an appropriate nutrient medium, whereby the desired polypeptide is produced and isolated from cells or from the medium, when the polypeptide is secreted. Where a host is employed in which the vector's transcriptional and translational regulatory signals are functional, then the DNA sequence of the Rf gene can be manipulated to provide for the expression of the desired polypeptide in proper juxtaposition to the regulatory signals. The polypeptide products can be obtained in substantially pure form, particularly free of cellular debris, which may include such contaminants as, for example, proteins, polysaccharides, lipids, nucleic acids, viruses, bacteria, fungi, and combinations thereof, using methods well known in the art.

The nucleic acids described above can be used in a wide variety of ways, depending upon their size, their natural function, the use for which they are desired, and the degree to which they can be manipulated to modify their function. For example, nucleic acids of at least about 20 bases, more usually at least 50 bases, and usually not exceeding about 10,000 bases, more usually not exceeding about 5,000 bases, may serve as probes for the detection of the presence of a nuclear restorer gene or homologous nucleic acid in an organism. Such detection can provide information relating to whether manipulation of the plant with a particular nuclear restorer gene can provide an opportunity to generate new varieties of the plant, and provide novel methods for the efficient production of hybrid seed.

The method of detection involves duplex formation by annealing or hybridization of the oligonucleotide probe, either labeled or unlabeled, depending upon the nature of the detection system, with the DNA or RNA of an organism believed to produce the particular nuclear restorer gene. Usually this method of detection involves cell lysis, extraction of nucleic acids with organic solvents, precipitation of nucleic acids in an appropriately buffered medium, and isolation of the DNA or RNA. Alternatively, one can amplify specific sequences via polymerase chain reaction (PCR). The DNA can be fragmented by mechanical shearing or restriction endonuclease digestion. The nucleic acid can then be bound to a support or can be used in solution, depending upon the nature of the protocol. The Southern technique (Southern, *J. Mol. Biol.*, 98, 503 (1975)) can be employed with denatured DNA by binding the single-stranded fragments, for example, to a nitrocellulose or nylon filter. RNA also can be blotted onto a filter (Thomas, *PNAS USA*, 77, 5201 (1980)). Preferably, the fragments are subjected to electrophoresis prior to binding to a support so as to enable the selection of variously sized fractions. Alternatively, the assay can be accomplished on plant cells fixed to a substrate and permeabilized by methods known in the art, whereupon the hybridization procedure can be conducted to determine if a homologous gene to a particular nuclear restorer gene exists in the plant of interest, and/or if that plant is expressing RNA that is homologous to the nuclear restorer gene.

The oligonucleotide probes can be DNA or RNA, albeit usually they are DNA. The oligonucleotide sequence can be prepared synthetically or by cloning. Suitable cloning vectors are well-known to those skilled in the art. The oligonucleotide probe can be labeled or unlabeled. A wide variety of techniques exist for labeling DNA and RNA and include radiolabeling by nick translation, random priming, tailing with terminal deoxytransferase, or the like, where the bases employed are labeled, for example, with radioactive $^{32}P$. Other labels, which can be used, include fluorophores, enzymes, enzyme substrates, enzyme cofactors, enzyme inhibitors, and the like. Alternatively, instead of using a label, which provides a detectable signal, by itself or in conjunction with other reactive agents, ligands can be used to which receptors bind, where the receptors are labeled, such as with the above-indicated labels, to provide detectable signals, by themselves or in conjunction with other reagents (see, e.g., Leary et al., *PNAS USA*, 80, 4045–4049 (1983)). The oligonucleotide probes are hybridized with the denatured nucleic acid, substantially intact or fragmented, or fractions thereof, under conditions of predetermined stringency, the practicalities of which have been discussed hereinabove.

In accordance with another aspect of the present invention, the nucleic acids disclosed herein are used in a method for the production of hybrid seed, comprising the steps of: (a) obtaining a nucleic acid comprising a nucleotide sequence that hybridizes to SEQ ID NOS:1, 3 or 4 under at least moderately stringent conditions and restores male fertility to a cytoplasmic male-sterile plant; (b) introducing the nucleic acid of (a) into a plant cell; (c) generating a plant from the plant cell of (b), which comprises and expresses the nucleic acid of (a); (d) pollinating a cytoplasmic male-sterile plant by the plant of (c); and (e) obtaining a seed, which generates a fertile plant, from the cytoplasmic male-sterile plant of (d). The nucleic acid of (a) preferably comprises SEQ ID NOS: 1, 3 or 4, a sequence complementary to any one of SEQ ID NOS: 1, 3 and 4, a sequence substantially equivalent to any one of SEQ ID NOS: 1, 3 and 4, and a sequence substantially equivalent to a sequence complementary to any one of SEQ ID NOS: 1, 3 and 4. The plant of (c), which is one of a line or variety of such plants, preferably can produce seeds; however, such seeds may or may not give rise to fertile plants. Accordingly, the inventive method involves plant tissue culture techniques known in the art.

Introduction of nucleic acids into a plant cell is accomplished by any suitable means, including cell bombardment, i.e., attaching the DNA to metallic pellets and blasting them through the plant's cell wall (Fromm et al., *Bio/Technology*, 8, 833–839 (1990); and Gordon-Kamm et al., *Plant Cell*, 2, 603–618 (1990)), and, for the introduction of exogenous DNA to a dicotyledonous plant cell, insertion of the nucleic acid of the present invention into the Ti plasmid of Agrobacterium and adding suitable ingredients to promote transformation thereby (Horsch et al., *Science*, 223, 496–498 (1984); and DeBlock et al., *EMBO J.*, 3, 1681–1689 (1984)). Other techniques are available for the introduction of exogenous DNA into a plant and/or a subset of its constituent cells, including electroporation, protoplast-mediated gene transfer, and silicon carbide crystal-mediated gene transfer. These various techniques are discussed in, for example, *Genetic Engineering News*, vol. 14, no. 4 (Feb. 15, 1994), pages 1, 3, and 24, and are generally known in the art. Accordingly, plants that comprise nucleic acids of the present invention can be generated by using tissue culture, wherein transformed or transfected cells are grown into plants, or by conventional gene transfer directly into a plant. This line of plants comprising and expressing a nucleic acid is then established using conventional breeding techniques.

The method is applicable to any plant, preferably any sexually reproducing plant, including plants of agronomic value, such as maize, soybean, alfalfa, wheat, rapeseed, rice, sorghum, beet, various vegetables including cucumber, tomato, peppers, and the like, various trees including apple, pear, peach, cherry, redwood, pine, oak, and the like, and various ornamentals. The plant is preferably maize, rapeseed, rice or sorghum.

Hybrid seed also can be produced in accordance with another aspect of the present invention. For purposes of setting forth the general method, Rf2 will be used as an example; the method, of course, is not limited to Rf2. Using methods generally known in the art, e.g., backcrossing, mutagenesis, or homologous recombination, a first plant, which is homozygous for a leaky mutant allele of Rf2 (or another housekeeping gene product present in the mitochondria, the chloroplast or cytosol), is generated. The leaky mutant allele can, for example, comprise minor amino acid substitutions that only slightly impair the function of the housekeeping gene product. Alternatively, the leaky mutants can arise via altered regulatory sequences, such that the gene product is present at somewhat less than optimal amounts. Such an allele should condition male fertility in a normal cytoplasm but cause or allow male sterility in certain novel cytoplasms. In addition, the leaky allele preferably hybridizes to a nucleic acid described above under at least moderately stringent conditions. A second plant, which comprises a "defective" cytoplasm due to one or more genetic defects, which condition male fertility in a completely wild-type nuclear genome, but male sterility in the presence of a nuclear genome homozygous for a leaky mutant Rf allele, is also generated, using such methods as described with respect to the first plant. The second plant is then crossed by, i.e., pollinated by, the first plant to obtain seeds, which generate fertile and sterile $F_1$ plants, from the second plant. $F_1$ seeds that produce sterile plants can be grown and backcrossed by plants like the above-described first plant to homozygosity for the leaky mutant alleles of Rf1 or Rf2. Plants with the defective cytoplasm and homozygous for the leaky allele will be male-sterile and, therefore, useful for the production of hybrid seed, as set forth herein above. Taking into consideration the possible detoxifying function of the Rf2 gene product, the same procedures can be followed wherein the housekeeping gene function is to restore the activity of a second gene product's activity by, for example, removing aldehyde groups that are destabilizing or otherwise improve the functioning of the second gene product.

In accordance with another aspect of the present invention, an RNA-processing encoding region of a gene from any organism, such as a snRNP- or U2AF-1-encoding region, can be coupled to a mitochondrial targeting sequence, such as the ATP synthase subunit 9 leader peptide from *Neurospora crassa* (Huang et al. (1990), supra), and introduced into a vector. One skilled in the art will recognize that a variety of leader sequences can be used, such as those from plants, animals, or fungi, to target the mitochondria. The snRNP- or U2AF-1-encoding region, for example, can be engineered to recognize a specific string of nucleotides representing a binding site, such as an RNA or protein biding site, e.g., 5'-CNACNNU-3' (SEQ ID NO: 7; and FIG. 1), in a cytoplasmic male sterility sequence. The vector then can be introduced into a plant cell and a first plant, which comprises and expresses the snRNP- or U2AF-1-encoding region of a gene, can be generated. A second plant, which is a cytoplasmic male-sterile plant and which comprises a cytoplasmic male sterility sequence comprising a nucleotide sequence recognized by the RNA-processing complex, such as a snRNP/U2AF-1 complex, is then crossed (as a female), i.e., pollinated, by the first plant. The RNA-processing complex, e.g., snRNP/U2AF-1 complex, then cleaves the cytoplasmic male sterility transcript at the specific binding site, and expression of the cytoplasmic male sterility sequence is suppressed in the progeny of the cytoplasmic male-sterile plant. Accordingly, fertility is restored.

The present invention also provides an organism comprising the vector comprising a nucleic acid comprising a nucleotide sequence as described above. A suitable organism can be any suitable plant, yeast, or bacterium, such as discussed herein above regarding suitable plants from which to isolate the restorer genes and regarding suitable hosts in which to insert the enriched or isolated nucleic acid of the present invention. Preferred organisms are sexually-reproducing plants, as described above. A seed-bearing plant that hosts a vector/nucleic acid construct can bear seeds, which, themselves, comprise the vector.

Also provided is a virus comprising the vector comprising a nucleic acid comprising a nucleotide sequence as described above. The virus can be a bacteriophage, for example.

Finally, a plant cell comprising a vector of the present invention constitutes another preferred embodiment. Such cells can be cultured and kept as plant tissue culture cells, or certain plant hormones known in the art can be added to the culture media, thereby causing the plant tissue culture cells to differentiate and thereby form a new plant variety. Such plant culturing methods useful in the performance of this aspect of the invention are well-known in the art. Such a new plant variety can be fertile or sterile.

The following examples further illustrate the present invention, but, of course, should not be construed as in any way limiting its scope.

EXAMPLE 1

This example illustrates the use of two different transposon systems in maize for the selection of lines of plants that carry male-fertility nuclear restorer genes.

The following populations of maize were used to map the chromosomal locations of the rf1 and rf2 genes. For further discussion of the sources of the populations of maize and the genetic crosses performed, see Wise et al., *Theor. Appl. Genet.*, 88, 785–795 (1994).

| Population | Cross type | No. of progeny | Parent 1 | Parent 2 | Traits scored |
|---|---|---|---|---|---|
| Rf1 | | | | | |
| 92 1267–68* | BC$_1$ | 96 | R213-T/g16 [Rf1rf1, rf2Rf2]♦ | g16-N [rf1rf1, Rf2Rf2] | Rf1-mediated male fertility |
| G16 | | | | | |
| 92 1140–43 | F$_2$ | 102▲ | Q66-N [G16G16] | g16-N [g16g16] | g16 |
| 92 2117–118 | | | | | |
| RG1 | | | | | |
| 92g 5029–63 | TC | 89 (6 selected)• | R213-T/Acc731 [Rf1rf1 rg1Rg1, rf2Rf2] | g16-N [rf1rf1 rg1rg1, Rf2Rf2] | Rf1-mediated male fertility Rg1 |
| RF2A | | | | | |
| 91g 6222–30 | BC$_1$ | 41 | R213-T [Rf1Rf1, rf2Rf2] | rf2-m 8904/ R213-N [rf1rf1, rf2Rf2] | Rf2-mediated male fertility |

Maize populations used for mapping rf1 and rf2 with RFLP and visible markers
-continued

| Population | Cross type | No. of progeny | Parent 1 | Parent 2 | Traits scored |
|---|---|---|---|---|---|
| RF2B | | | | | |
| 92 1101–05 | BC$_1$ | 903 (86 evaluated for RFLP markers) | R213-T/wx-m8 [rf1Rf1, Rf2rf2] | R213-N [Rf1Rf1, rf2rf2] | Rf1- and Rf2-mediated male fertility |

*Pedigree numbers associated with this population
♦Parental genotype. See Wise et al. (1994), supra.
▲Selected for homozygous g16.
•Ragged, male-fertile plants, carrying a recombination between the rg1 and rf1 loci were selected.

By analyzing restriction fragment length polymorphisms (RFLP) in accordance with conventional methods (see Sambrook et al. (1989), supra), rf1 and rf2 were mapped to positions on chromosomes 3 and 9, respectively, as set forth below.

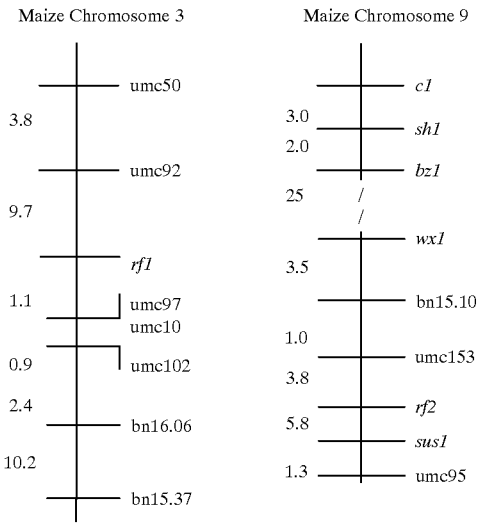

The RFLP maps of maize chromosomes 3 and 9, along with other such maps, were used in crosses between a transposon-carrying line and a genetically marked nontransposon line to determine the position of a transposon on a given chromosome by insertional mutagenesis as evidenced by analysis of RFLP and visible markers. Accordingly, stocks carrying certain transposon systems, i.e., Mutator, Cy, or Spm, were crossed to genetically marked nontransposon lines in order to tag the Rf1 and Rf2 genes (see Walbot, *Ann. Rev. Plant Physiol. Plant Mol. Biol.*, 43, 49–82 (1992)). Specifically, Rf2 was tagged in the following cross, which was carried out in an isolation plot using the method of Peterson (In *Maize Breeding and Genetics* (D. B. Walden, ed., John Wiley & Sons, New York, N.Y., 1978), pages 601–631) (the female parent is listed first in all crosses herein):

Cross 1: T Rf1/Rf1 rf2 wc1/rf2 wc1 (inbred R213)×N rf1/rf1 Rf2 wc1/Rf2 wc1 Mutator Cross 2: T Rf1/Rf1 rf2 wc1/rf2 wc1 (inbred R213)×N rf1/rf1 Rf2 wc1/Rf2 wc1 Cy Cross 3: T Rf1/Rf1 c Sh Bz1 Wx1 rf2/c Sh Bz1 Wx1 rf2 (inbred R213)×N rf1/rf1 c1-m5 Sh B z1 wx1-m8 Rf2/c Sh Bz1 wx1 Rf2

In the absence of mutation, progeny kernels from each cross are heterozygous for the wild-type Rf allele and should, therefore, yield wild-type, i.e., male-fertile, plants. However, if a gamete from the transposon-carrying parent carries a mutant Rf allele generated by insertional mutagenesis of the transposon at (i.e., within or immediately adjacent to) the Rf locus, the progeny kernels are heterozygous for the mutant: Rf allele, designated rf-m (i.e., rf1-m for Rf1 and rf2-m for Rf2), and should, therefore, yield mutant, i.e., male-sterile, plants.

The results of these crosses, including population source, size, and mutation rate, are as follows:

| Population | Subpopulation | Transposon donor source* | No. of rf2-m alleles isolated | Population size | Mutation rate no./100,000 gametes |
|---|---|---|---|---|---|
| Mutator | YA | Mu$^4$ outcross (1220) | 1 | 8,500 | |
| | P | Mu$^2$ outcross (1120) | 1 | 12,000 | |
| | G | Mu$^1$ outcrosses (1212, 1215, 1218, 1219) | 3 | 5,000 | |
| | OB | Mu$^2$ outcross (1118) | 0 | 12,000 | |
| | B | Mu$^2$ outcross (1121, 4938) | 0 | 9,700 | |
| | M | Mu outcrosses (1207, 1216, 1222, 1224) | 0 | 3,100 | |
| Mutator population total | | | 5 | 50,300 | 9.9 |
| Cy | OA/BB | 1230–1234, 3919–3921 | 1 | 28,000 | |
| Cy population total | | | 1 | 28,000 | 3.6 |
| Spm | CV | Revertants from c1-m5 | 0 | 20,000 | |
| | c1-m5 | "Control" | 1 | 80,000 | |
| Spm population total | | | 1 | 100,000 | 1.0 |

*Transposon donor sources are indicated by the pedigree numbers, Mu outcross, Mu$^2$ outcross, and Mu$^4$ outcross are defined by Robertson, Mol. Gen. Genet., 191, 86–90 (1983).

Seven heritable rf2-m alleles were derived from the above-described Mutator and Spm transposon stocks. The progenitor allele for each of the seven rf2-m alleles is as follows:

| Allele | Progenitor Allelle |
|---|---|
| 8110 | Q67 |
| 8122 | Q66 |
| 9323 | Q66 |
| 9385 | not determined |
| 9390 | Q67 |
| 9437 | Q67 |
| 8904 | not determined |

Accordingly, transposon-generated mutants at the Rf2 genetic locus were obtained for use in isolating the Rf2 gene and/or cDNA.

EXAMPLE 2

This example illustrates the isolation of the Rf2 gene from the rf2-m lines described in Example 1.

A Mu1 transposon was shown to cosegregate with one of the alleles identified in Example 1 and Schnable et al., *Genetics*, 136, 1171–1185 (1994), i.e., rf2-m8122. Cosegregation analysis was performed on a representative subset of 56 male-sterile (rf2-m8122/rf2-ref) and 49 male-fertile siblings (Rf2/rf2-Rf2/rf2-ref) from two segregating families derived from the cross: T cytoplasm Rf1/Rf1 rf2-R213/rf2-R213×Rf1/Rf1 Rf2/rf2-m8122. A 3.4 kilobase, Mu1-hybridizing Eco RI/Hin dIII restriction fragment was present in male-sterile siblings, but absent from male-fertile siblings in both of these segregating families.

Using standard recombinant DNA techniques, total DNA from a single male-sterile plant that carried rf2-m8122 was subjected to preparative Eco RI/Hin dIII digestion and size-selected DNA was isolated for ligation into the lambda phage vector NM 1149 (Murray, *The Bacteriophage Lambda*, Hendrix, ed. (1983)). The 3.4 kilobase Eco RI/Hin dIII fragment released from a Mu1-positive lambda phage (named λ91 8122 #9) isolated from the resulting library was subcloned into the plasmid vector pBSK or pBKA (Stratagene), and named prf2. The prf2 plasmid was used to transform *E. coli* DH5α or XL1-Blue MRF', and named PF#9. A restriction site map of the insert of the pRf2 plasmid is shown in FIG. 2, wherein H stand s for Hin dIII, D stands for Dra I, Hc stands for Hin cII, P stands for Pst I, Bg stands for egt II, and E stands for Eco RI. The location of the Mu1 insertion point is clearly marked as between the second Dra I and Bgl II restriction sites. Hybridization of the radiolabeled pRf2 fragment #1 to maize genomic DNA established that the cloned DNA was derived from the 3.4 kb Mu1-hybridizing Eco RI-Hin dIII fragment present in male-sterile but not male-fertile siblings.

EXAMPLE 3

This example illustrates the verification of the identity of the Rf2 clone of Example 2.

The identity of the Rf2 genomic clone described above was confirmed by allelic cross-referencing experiments. A single-copy fragment from pRf2 (i.e., rf2 probe #1, FIG. 2) was hybridized to DNA derived from five independent rf2 mutants and their respective wild-type progenitor alleles as recited in Example 1. The results revealed polymorphisms between each rf2-m allele and its corresponding wild-type progenitor allele. Specifically, the rf2-m8122 allele was associated with a slower-moving restriction fragment (i.e., a fragment with lower gel electrophoretic mobility) than was the progenitor Q66 allele. Similarly, rf2-m8110 differed from its progenitor Q67, rf2-m9323 differed from its progenitor Q66, and rf2-m9390 differed from its progenitor Q67. The results confirmed that pRf2 included at least a portion of the sequence of the Rf2 gene.

EXAMPLE 4

This example illustrates the nucleotide sequence of the Rf2 insert of a cDNA clone identified using the insert of the pRf2 plasmid, as discussed in Example 2. Additionally, this example illustrates the comparison of the rf2 cDNA nucleotide sequence with those sequences stored in publicly available gene databases.

Using $^{32}$P-radiolabeled rf2 probes #1 and #2 (shown in FIG. 2) in combination, a cDNA library derived from mRNA isolated from immature maize tassels and cloned into λGT10 phage was screened, using methods well-known in the art (see Sambrook et al. (1989), supra; the cDNA library, named ts2, was a gift of S. Delaporta of Yale University). From a first screen, six putative positive plaques of phage were identified, which, upon a series of two rescreenings, were resolved to include three verified positive plaques. DNA from the positive phage was analyzed for its ability to hybridize to probes #1 and #2. In addition, the sizes of the inserts were determined. The phage having the largest insert was selected for subcloning into plasmids pBSK and pBKA (Stratagene) for sequencing. The cDNA clone used for sequencing was named rf2 cDNA 6-2-8-1.

Using conventional nucleic acid sequencing methods (Sambrook et al. (1992), supra), the partial 5' sequence of the insert of the rf2 cDNA clone 6-2-8-1 was determined to be:

```
  1 CTTTTCCTCT TCTGATGTAT GCCTGGAAAG TTGGCCCTGC TTTGGCATGT [SEQ ID NO:1]

51 GGAAATACTC TCGTGCTCAA GACTGCTGAA CAAACCCCTC TATCGGNTTT

101 GTATATCTCC AAATTGTTGC ATGAGGCTGG ACTACCTGAG GGTGTTGTGA

151 ATGTCGTTTC TGGTTTTGGN CCTACTGCTG GTGCTGCTCT TGCTAGTCAC

201 ATGGATGTTG ATAAGATCGC ATTTACTGGA TCTACCGATA CTGGAAAAAT

251 TATTCTCGAG TTGGCTGCAA AGAGCAACCT TAAGACAGTG ACACTGGAGT

301 TAGGAGGAAA GTCCCCTTTC ATCATATGGA CGAAGCTGAT GTTTGGACCA

351 GCTNTTGGAG CTTGNGCANC TTGGCCTGTN CTTTTACCAG GANAATGCTG

401 TA
```

Using the National Center for Biotechnology Information (NCBI) Experimental GENINFO® BLAST Network service (Blaster), SEQ ID NO:1 and a translated corresponding amino acid sequence of SEQ ID NO:1 (i.e., SEQ ID NO:2) were compared to the amino acid sequences included in at least the following databases: (1) Brookhaven Protein Data Bank, April 1994 Release; (2) SWISS-PROT, Release 30.0, October 1994, Release 41.10 (complete), Sep. 19, 1994; (3) GenBank®, Release 85.0 Oct. 15, 1994; (4) Kabat Sequences of Proteins of Imunological Interest, Release 5.0, August: 1992; (5) TFD transcription Factor (protein) Database, Release 7.0, June 1993; (6) Ancient Conserved Region subset of SWISS-PROT Dec. 3, 1993; (7) Translations of select Alu repeats from REPBASE NUCLEOTIDE SEQUENCE DATABASES; (8) EMBL Data Library, Release 40.0, September 1994; (9) Vector subset of GenBank® 82.0, Apr. 11, 1994; (10) Kabat Sequences of Nucleic Acids of Immunological Interest, Release 5.0, August 1992; (11) Eukaryotic Promotoer Database, Release 35, June 1993; (12) Database of Expressed Sequence Tags (cumulative daily update); and (13) Database of Sequence Tagged Sites, Release 1.5, Oct. 26, 1994. In all, more than 132,000 sequences are contained in these databases.

The results of the computer database search indicated that the Rf2 gene is highly related to aldehyde dehydrogenase from a variety of species, including Bos taurus (73% homology), Ovis aries (73% homology), horse (74% homology), Aspergillus niger (86% homology), and Homo sapiens (86% homology). In particular, SEQ ID NO:1 shares substantial homology with both mitochondrial and cystolic aldehyde dehydrogenase from human, rat, Aspergillus n., and other species. It appears, therefore, that Rf2 encodes a common enzymatic function, aldehyde dehydrogenase, which can be viewed as a necessary mitochondrial activity, and/or which can be viewed as a necessary detoxifying activity to restore a vital mitochondrial activity.

EXAMPLE 5

This example demonstrates the use of the cloned Rf2 gene.

The present invention can be used to generate multiple CMS systems, which can be mixed in the same manner as the C, S and T systems are now, thereby providing a greater variety of genetic backgrounds for hybrid seed production. Because Rf2 appears to encode a common enzymatic function, aldehyde dehydrogenase, "leaky" mutations (such as that presumably carried by the rf2-ref allele) are not phenotypically expressed in a normal cytoplasm. For example, an N-cytoplasmric rf2/rf2 plant is male-fertile. However, in a male-sterile cytoplasm, such as T, which is already "weakened," the rf2 mutation and the cytoplasmic mutation, in combination, effectively result in male sterility. Accordingly, an existing male-sterile cytoplasm, such as C, S or T, or a mutated cytoplasm and a mutant or mutated gene, like rf2, which is associated with a mitochondrial or cytosolic function, are combined. In combination, these two mutations serve as a CMS/restorer system. Any number of CMS/restorer systems can be made and used in any species. This broad cross-species applicability of the present invention is evident in view of the degree of homology between SEQ ID NO: 1 of maize and nucleic acid sequences encoding proteins in such an evolutionarily divergent organism as the cow.

In addition, "strong" mutants (e.g., complete loss of function) of rf2 can be generated so as to render a normal cytoplasm phenotypically male-sterile (upon self-pollination). An example of such an allele is one of the transposon-induced alleles described in Schnable et al., Genetics, 136, 1171–1185 (1994). Such alleles can be used, for example, in the Pioneer system described above.

Accordingly, the Rf genes identified herein are useful in the production of hybrid seed and enable the utilization of a broader gene pool in the cultivation of plants of agronomic (or ornamental) value.

EXAMPLE 6

This example illustrates the tagging of the Rf1 gene.

Rf1 clones were isolated as described for the isolation of Rf2 clones, i.e., a transposon-carrying line was used to tag the Rf1 gene. It is necessary to use linked markers (as identified in the map of Maize Chromosome 3 above) to distinguish between the newly induced mutants and the recessive allele used to uncover them. To facilitate this approach, five rf1 inbreds (W22, B37, Mo17, W64A and B73) were RFLP-fingerprinted for chromosome 3. Their respective DNAs were digested with 8 restriction endonucleases (Bam HI, Eco RI, Eco RV, Hin dIII, Kpn I, Dra I, Bcl I, and Bgl II), followed by Southern analyses with RFLP markers that flank rf1, in order to identify an rf1 donor line with distinctive RFLP alleles flanking rf1. By so doing, it was established that rf1-B37 can easily be distinguished from the Rf1Ky21 or Rf1-IA153 (present in the Wf9-BG inbred) alleles present in the Mutator population by using the restriction enzyme Dra I in conjunction with umc10 and umc92, which flank rf1 (see above).

Using the above strategy and materials, Mutator-induced male-sterile mutants of the rf1 fertility-restorer locus were identified. The Rf1/Rf1 Mutator lines were crossed by the inbred line B37, which has the genotype rf1/rf1, Rf2/Rf2, thereby providing Cross 4:

T Rf1/Rf1 (Mutator)×N rf1-B37/rf1-B37.

The parents used in Cross 4 and all subsequent crosses were homozygous for Rf2.

In the absence of mutation, the progeny from cross 4 are male-fertile because, although they have T cytoplasm, they carry at least one copy of each of the two dominant nuclear restorer factors, Rf1 and Rf2. However, if, with respect to a given progeny, the Rf1 locus was inactivated by insertion of a Mu element, then that plant would be male-sterile. These exceptional plants putatively carry Mutator-induced rf1-m alleles. Progeny of Cross 4 (~=123,500) were screened for mutations at rf1; ten putative male-sterile mutants were identified (Wise et al., *Genetics*, 143, 1383–1394 (July 1996)).

To confirm if the putative male-sterile mutants were heritable and to determine if the male-sterile phenotype was associated with the rf1 locus, the putative male-sterile mutants from Cross 4 (with the predicted genotype of T cytoplasm, rf1-m/rf1-B37, Rf2/Rf2) were crossed as shown in Cross 5:

T rf1-m rg1+/rf1-B37 rg1+×T Rf1 Rg1/rf1 rg1+, wherein rg1+ refers to the normal wild type allele found in most maize lines. Plants with the genotype rf1-M rg1+/Rf1 Rg1 were predicted to constitute 25% of the progeny from Cross 5 and were identified by the ragged phenotype and previously characterized DNA polymorphisms at chromosome 3 of each of Wf9-BG, Ky21, B37 and the previously described Rf1 Rg1 stock. Based on their pedigree, rf1-m alleles were expected to couple with Ky21- and/or Wf9-BG-derived RFLP markers, which are easily distinguished from those flanking the rf1 allele in B37. Plants derived from Cross 5 and having this target genotype were crossed as males onto T-cytoplasmic W64A females (rf1/rf1 Rf2/Rf2, see cross 6) as follows: Cross 6: T rf1/rf1 (W64A)×T rf1-m rg1+/Rf1 Rg1. Heritable, male-sterile mutations from Cross 6 were expected to segregate 1:1 (male-sterile : male-fertile), whereas non-heritable, male-sterile "mutants" were expected to be male-fertile. If the male-sterile mutation were at the rf1 locus, male-sterile plants would be normal and male-fertile plants would be ragged (except for rare crossovers). Four of the ten putative male-sterile mutants described above were shown to represent rf1-m alleles.

The families resulting from Cross 6 and carrying rf1-m3207 and rf1-m3310 segregated 1:1 for male-sterile, normal plants (rf1-m rg1+/rf1-B37 rg1+) and male-fertile, ragged (Rf1 Rg1/rf1-B37 rg1+) plants. DNA from each individual sibling was digested for cosegregation analysis with Hin dIII and/or Eco RI. Southern blots of the digested DNA were then probed with radiolabeled Mu1-specific sequences. For each of these rf1-m alleles, a Mu1-containing DNA fragment was identified that cosegregated with the mutant allele in over 40 progeny and, therefore, had a higher probability of representing Rf1 sequences. These DNA fragments were then cloned using procedures described in Example 2, and related procedures well-known in the art. Allelic cross-referencing experiments, as described above in Example 3, were then used to establish that the cloned sequences, indeed, represented Rf1.

EXAMPLE 7

This example describes the cloning of the rf1-m3207 allele and the isolation of Rf1-containing sequences.

Figure 3:
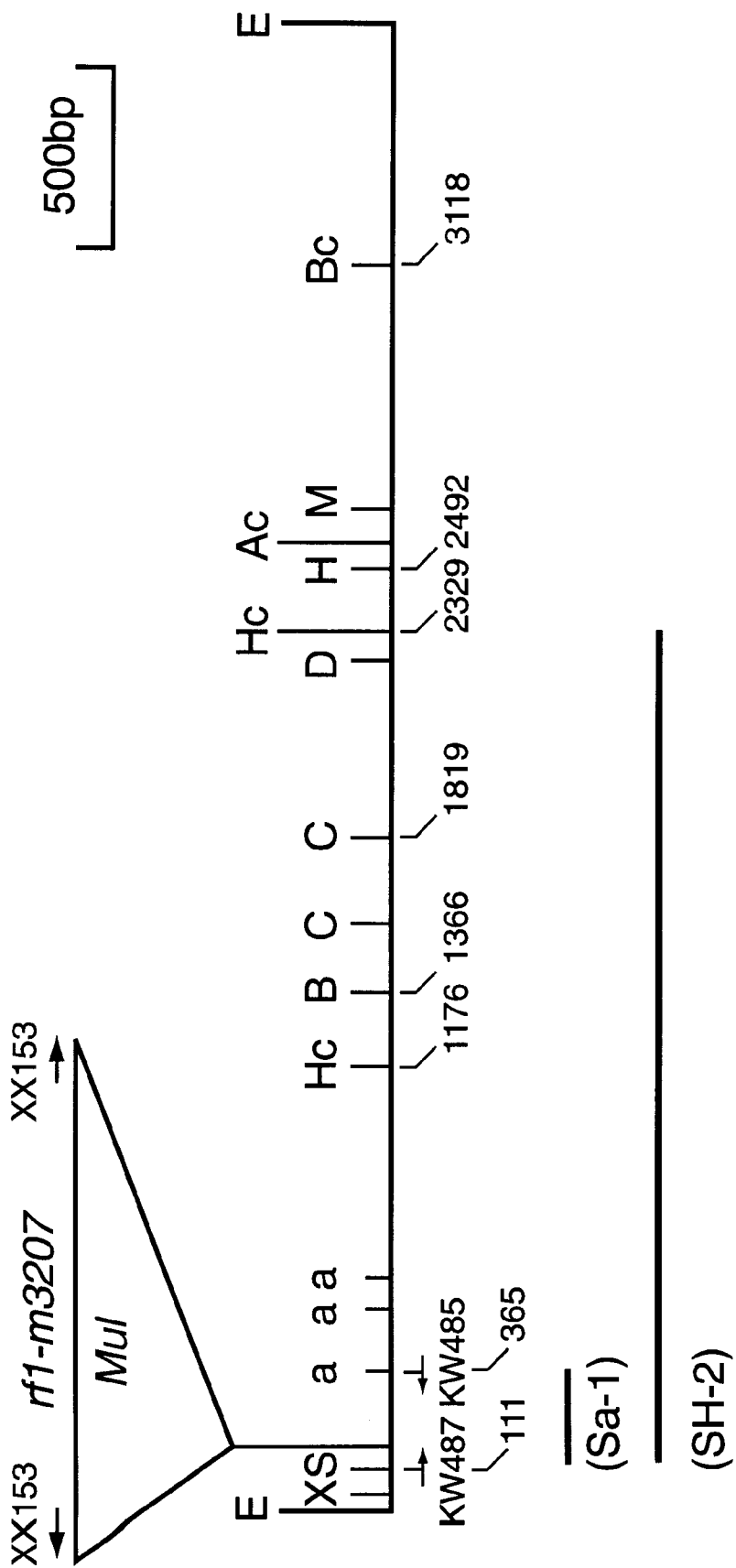
FIG. 3 is a restriction endonuclease map of the genomic clone prf1-m3207.

In DNA gel blot cosegregation analyses, the rf1-m3207 and rf1-m3310 alleles cosegregated with 5.5- and 2.4-kb Mu1-hybridizing Eco RI restrictions fragments, respectively, suggesting that they contained Mu transposon insertions in the Rf1 gene (Wise et al. (1996), supra). Following these analyses, total DNA from single male-sterile plants carrying the rf1-m3207 and rf1-m3310 alleles were subjected to preparative Eco RI digestion and size-selected DNA was isolated for ligation into the Eco RI site of Lambda ZapII (Stratagene, La Jolla, Calif.). Ligations were packaged with Gigapack III Gold packaging extracts (titres ranged from $2\times10^8$ to $1\times10^9$ pfu/µg) and plated onto NZCYM agar in 24×24 cm sterile Petri plates (Nunc) with Mg-top agarose and incubated at 37° C. until the plaques were visible (7–8 hr). Plaques were lifted onto Hybond N+ and hybridized with a random-primed Mu1 probe. Mu1-hybridizing plaques were purified and Bluescript phagemids were excised in vivo from the Lambda ZapII vector by the rapid excision procedure (Strategene, La Jolla, Calif.). Plasmid clones were subsequently transformed into the Sure strain of *E. coli* and restriction maps of the inserts were constructed. The restriction map of the 5.5 kb prf1-m3207 genomic clone is shown in FIG. 3, wherein the position of Sa-1, sequences representing a 254-bp Sac I-Alu I fragment, and SH-2, sequences representing a 2218-bp Sac I-Hin cII fragment, are illustrated below the map (E, Eco RI; X, Xho I; S, Sac I; a, Alu I; Hc, Hin cII; B, Bam HI; C; Cla I; D, Dra I; H, Hin dIII; Ac, Acc I; M, Mlu I; Bc, Bcl I. XX153 is an olignucleotide primer representing the Mu terminal inverted repeat sequence. KW487 and KW485 are primers that were used to amplify Sa-1. The low copy sequence, Sa-1, was amplified via PCR from Wf9-BG progenitor DNA with the KW487 and KW485 primers. The amplification product, which represents a 254-bp Sac I-Alu I fragment flanking the Mu1 insertion site in prf1-m3207, was used in DNA gel blot hybridization analyses to establish that the prf1-m3207 clone cosegregates with rf1 locus. In contrast, although the 2.4-kb Mul-hybridizing Eco RI restriction fragment is linked to the rf1-m3310 allele, as indicated below, it does not appear to represent Rf1 sequences.

To identify a cDNA representing the Rf1 gene, sequences flanking the Mu1 insertions in prf1-m3207 and prf1-m3310 were hybridized with approximately $1\times10^6$ independent clones from a cDNA library constructed from Wf9-BG seedling RNA carrying the Rf1-IA153 progenitor allele. Four classes of cDNAs were identified by hybridization with sequences derived from prf1-m3207; one was identified by hybridization to sequences from prf1-m3310. Sequences isolated from the five cDNA clones were used in DNA gel blot cosegregation analyses to determine whether or not they mapped to the rf1 locus. Of these five cDNAs, a probe representing nts 2077–2451 from the 3' end of the p6140-1 cDNA SEQ ID NO: 4 hybridized to a unique 10-kb Eco RI restriction fragment that cosegregated with rf1-m3310-mediated sterility in 83 progeny derived from cross 6. This hybridization pattern also established that the 10-kb Eco RI restriction fragment was present in the original plant carrying the rf1-m3310 allele, which was the parent of the cosegregation population, but absent from the Wf9-BG progenitor. Hence, a DNA sequence rearrangement detected by the p6140-1 cDNA (which was originally identified via its hybridization with the prf1-m3207-derived SH-2 probe; see FIG. 3) occurred in plant 93 3310 coincident with a mutation from Rf1 to rf1, but not in Wf9-BG. Because mutations at the rf1 locus coincided with DNA sequence rearrangements detected by p6140-1, this cDNA clone hybridizes to at least a portion of the Rf1 gene.

Comparison of the hybridization patterns of Sa-1, a low copy DNA sequence flanking the Mu1 insertion of prf1-m3207 and the probe representing nts 2077–2451 from the 3' end of the p6140-1 cDNA, established that the rf1-m3207- and rf1-m3310 alleles were on distinct 5.5 and 10 kb Eco RI restriction fragments. Therefore, although the 2.4 kb Eco RI Mu1-hybridizing fragment was linked to the rf1-m3310 allele, these analyses revealed that it probably did not represent part of the Rf1 gene. For this reason, further analyses focused on the p6140-1 cDNA clone.

EXAMPLE 8

This example describes the nucleotide sequence and the predicted amino acid sequence of the Rf1 cDNA and its homology to snRNP E.

Using conventional methods of nucleic acid sequencing, the sequence of the Rf1 cDNA clone was determined to be that of SEQ ID NO: 4. Twenty six elements of the predicted amino acid sequence of the Rf1 cDNA (nt 1468–1545 of p6140-1 (SEQ ID NO: 5)) revealed 96% homology and 69% identity with mammalian small nuclear ribonucleoprotein E (snRNP E) (SEQ ID NO: 6) as shown in FIG. 4.

The snRNP E protein is one of four "core" proteins associated with the snRNAs of the U (uridine-rich) family (U1, U2, U4, U5, and U6). These proteins are involved in RNA processing. Early reports had hypothesized such a function for the Rf1 gene product (Dewey et al. (1987), supra; Kennell et al. (1987), supra; and Kennell and Pring, Mol. Gen. Genetics, 216, 16–24 (1989)) although rigorous biochemical experiments had not demonstrated this conclusively. Hence, based on these preliminary data, one of the domains of the Rf1 gene product may function in the recognition and specificity of the Rf-associated processing sites of T-urf13 transcripts.

Other significant portions of predicted amino acid similarity to the p6140-1 cDNA were to hypothetical protein 1 of the En/Spm transposable element system of maize (Rf1 6140-1 cDNA nucleotides 2–262; 73% homology, 47% identity) and En/Spm mosaic protein (Rf1 6140-1 cDNA nucleotides 316–582; 47% homology, 31% identity). Nucleotides 2–262 also had substantial similarity to other known transposable element systems from *Glycine max* (soybean) and *Antirrhinum majus* (garden snapdragon), though one skilled in the art recognizes that all of these transposable element systems are similar to one another.

The last amino acid sequence similarity [revealed in the 3' region of the Rf1 6140-1 cDNA, (nucleotides 1761–2357; 42–100% identity)] was to pMS18 (EMBL locus ZMFS18; accession A01387, X67324), a cDNA that had a predicted amino acid sequence similar to other plant structural proteins, eg., barley (EMBL accession 629788; Wright et al., Plant J., 3(1), 41–49 (1993)).

The above results suggested that the Rf1 mRNA may be chimeric, a result that would be consistent with predictions that Rf1 represents a neomorphic allele (Wise et al. (1996), supra). Due to the diverse nature of the individual motifs within the Rf1 p6140-1 cDNA, we predicted that this mRNA may originate via recombination between different domains from different genes. One test of this hypothesis was performed as follows. A DNA restriction fragment representing the region homologous to snRNP E (nucleotides 1355–1543) was isolated via double digestion of the p6140-1 cDNA with Mlu I and Bgl II. Sequences representing the plant structural-gene homologue (nucleotides 2077–2451) were amplified via polymerase chain reaction. Both of these fragments were used as individual hybridization probes on the original Wf9-BG cDNA library filters. Fourteen positive plaques (out of 400,000) hybridized to the snRNP E horiologue probe and more than 500 hybridized to the plant structural-gene homologue probe at high stringency. Except for hybridization to the original p6140-1 plaque, the two groups of the hybridizing plaques were mutually exclusive. All of the inserts identified via hybridization to the snRNP E homologue were of distinct size classes, whereas almost all of the inserts identified via hybridization to the plant structural-gene homologue were nearly identical. Additionally, the snRNP E probe hybridized to multiple restriction fragments on DNA gel blots of total maize DNA whereas the structural protein probe hybridized to low-copy sequences. These results suggested that the fourteen clones identified via hybridization to the snRNP E homologue may be discrete, yet related sequences, whereas the abundance of clones identified via hybridization to plant structural protein homologue may be identical but originate from one or two highly expressed sequences in etiolated seedlings, the tissue source of the Wf9-BG cDNA library. Eight plaques identified by each hybridization were purified, plasmids excised, and sequenced. Sequence alignment analyses suggest that the Rf1 mRNA is a true chimera with one of the recombination breakpoints (between four cDNAs identified via hybridization to the snRNP E homologue and eight cDNAs identified via hybridization to the plant structural-gene homologue) at nucleotide 1545.

A short segment of the predicted amino acid sequence of a second cDNA clone identified via hybridization to the SH-1 sequence of prf1-m3207 (p6140-3) exhibited similarity to U2AF-1 (U2 small nuclear ribonucleoprotein auxiliary factor), which is also involved in RNA splicing. The essential eukaryotic pre-mRNA splicing factor U2AF-1 is required to specify the 3' splice site at an early step in spliceosome assembly. The two cDNAs p6140-1 and p6140-3 are 100% identical for 395 nucleotides, which also align with the prf1-m3207 genomic sequence.

All of the references cited herein, including patents, patent applications, and technical literature, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An enriched or substantially isolated nucleic acid comprising (i) the plant-derived nucleotide sequence of SEQ ID NO: 4, (ii) the nucleotide sequence complementary to the nucleotide sequence of SEQ ID NO: 4, (iii) the nucleotide sequence of SEQ ID NO: 4 comprising one or more neutral or conservative mutations in a region other than that corresponding to nucleotides 1468–1545 of SEQ ID NO: 4, (iv) the nucleotide sequence complementary to the nucleotide sequence of SEQ ID NO: 4 and comprising one or more neutral or conservative mutations in a region other than that corresponding to nucleotides 1468–1545 of SEQ ID NO:4, wherein said nucleotide sequence restores male fertility to a cytoplasmic male-sterile plant, or (v) a continuous fragment of any of (i)–(iv) wherein said fragment comprises nucleotides 1468–1545 of SEQ ID NO:4 or the complementary sequence thereto and restores male fertility to a cytoplasmic male-sterile plant.

2. The nucleic acid of claim 1, wherein said plant is selected from the group consisting of maize, soybean, petunia, common bean, rapeseed, canola, cotton, safflower, peanut, palm, sorghum, rice, wheat, alfalfa, beet and sunflower.

3. The nucleic acid of claim 1, wherein said plant is selected from the group consisting of maize, rapeseed, rice, petunia, common bean, sunflower and sorghum.

4. A vector comprising a nucleic acid of claim 1 as an insert.

5. A method of producing hybrid seed, which method comprises:

(a) obtaining an enriched or substantially isolated nucleic acid comprising a nucleotide sequence that hybridizes under at least moderately stringent conditions to SEQ ID NO:4 and restores fertility to a cytoplasmic male-sterile plant;

(b) introducing said nucleic acid into a plant cell;

(c) generating a plant from the plant cell of (b), which comprises and expresses the nucleic acid of (a);

(d) pollinating a cytoplasmic male-sterile plant by the plant of (c); and (e) obtaining a seed, which generates a fertile plant, from the cytoplasmic male-sterile plant of (d).

6. The method of claim 5, wherein said nucleic acid comprises (i) the plant-derived nucleotide sequence of SEQ ID NO: 4, nucleotide sequence complementary to the nucleotide sequence of SEQ ID NO: 4, (iii) the nucleotide sequence of SEQ ID NO: 4 comprising one or more neutral or conservative mutations in a region other than that corresponding to nucleotides 1468–1545 of SEQ ID NO: 4, (iv) the nucleotide sequence complementary to the nucleotide sequence of SEQ ID NO: 4 and comprising one or more neutral or conservative mutations in a region other than that corresponding to nucleotides 1468–1545 of SEQ ID NO:4, or (v) a continuous fragment of any of (i)–(iv) wherein said fragment comprises nucleotides 1468–1545 of SEQ ID NO:4 or the complementary sequence thereto and restores male fertility to a cytoplasmic male-sterile plant.

7. The method of claim 5, wherein said plant is selected from the group consisting of maize, rapeseed, rice, and sorghum.

8. An organism comprising the vector of claim 9.

9. The organism of claim 8, wherein said organism is selected from the group consisting of a plant, a yeast, and a bacterium.

10. A virus comprising the vector of claim 4.

11. The virus of claim 10, wherein said virus is a bacteriophage.

12. A seed comprising the vector of claim 4.

13. A plant cell comprising the vector of claim 4.

14. A plant comprising the vector of claim 4.

15. A method of producing hybrid seed, which method comprises:
  (a) generating a first plant, which is homozygous for a leaky mutant allele of Rf1, wherein Rf1 comprises SEQ ID NO:4, or a leaky mutant allele of Rf2, wherein Rf2 comprises SEQ ID NO:1 or 3;
  (b) generating a second plant, which comprises a defective cytoplasm;
  (c) pollinating the second plant by the first plant; and
  (d) obtaining a seed, which generates a fertile plant, from the second plant.

16. A method of producing a variant of a cytoplasmic male-sterile plant, which method comprises:
  (a) generating a first plant, which is homozygous for a leaky mutant allele of Rf1, wherein Rf1 comprises SEQ ID NO:4, or a leaky mutant allele of Rf2, wherein Rf1 comprises SEQ ID NO:1 or 3;
  (b) generating a second plant, which comprises a defective cytoplasm;
  (c) pollinating the second plant by the first plant;
  (d) obtaining a seed, which generates a male-sterile plant, from the second plant;
  (e) generating a male-sterile plant from the seed of (d); and
  (f) backcrossing the male-sterile progeny of the male-sterile plant of (e) by a plant like the plant of (a) until a plant, which is homozygous for the leaky mutant allele of Rf1 or Rf2, is obtained.

17. A method of suppressing cytoplasmic male sterility in the progeny of a cytoplasmic male-sterile plant, which method comprises:
  (a) obtaining a vector comprising an RNA-processing encoding region of a gene coupled to a mitochondrial targeting sequence;
  (b) introducing the vector of (a) into a plant cell;
  (c) generating from the plant cell of (b) a plant, which comprises and expresses the vector of (a);
  (d) pollinating a cytoplasmic male-sterile plant, which comprises a cytoplasmic male sterility sequence comprising a nucleotide sequence recognized by the RNA-processing complex encoded in the vector of (a), by the plant of (c); and
  (e) suppressing expression of the cytoplasmic male sterility sequence in the progeny of the cytoplasmic male-sterile plant of (d).

18. The method of claim 17, wherein said RNA-processing encoding region of a gene is selected from the group consisting of a snRNP-encoding region and a U2AF-encoding region.

19. A vector comprising a nucleic acid as an insert, wherein said nucleic acid comprises (i) the nucleotide sequence of nucleotides 1468–1545 of SEQ ID NO:4, (ii) the nucleotide sequence complementary to the nucleotide sequence of nucleotides 1468–1545 of SEQ ID NO:4, (iii) the nucleotide sequence of nucleotides 1468–1545 of SEQ ID NO:4 comprising one or more neural or conservative mutations, (iv) the nucleotide sequence complementary to the nucleotide sequence of SEQ ID NO:4 and comprising one or more neutral or conservative mutations, wherein said nucleotide sequence restores male fertility to a cytoplasmic male-sterile plant, or (v) a continuous fragment of any of (i)–(iv) wherein said fragment comprises nucleotides 1468–1545 of SEQ ID NO:4 or the complementary sequence thereto and restores male fertility to a cytoplasmic male-sterile plant.

20. An organism comprising the vector of claim 19.
21. A virus comprising the vector of claim 19.
22. The virus of claim 21, wherein said virus is a bacteriophage.
23. A seed comprising the vector of claim 19.
24. A plant cell comprising the vector of claim 19.
25. A plant comprising the vector of claim 19.
26. The method of claim 17, wherein said vector comprises nucleotides 1468–1545 of SEQ ID NO:4.

* * * * *

UNITED STATES PATENT AND TRADEMARK OFFICE
CERTIFICATE OF CORRECTION

PATENT NO.   :  5,981,833
DATED        :  November 9, 1999
INVENTOR(S)  :  Roger P. Wise; Patrick S. Schnable It is certified that errors appear in the above-identified patent and that said Letters Patent is hereby corrected as shown below:

ON THE TITLE PAGE:

In Assignees: "Washington, D.C." should read --Peoria, IL--

In Column 4, line 42: "is" should read --ms--

In Column 5, line 25: "(d)" should read --(d).--

In Column 7, line 35: "welting" should read --melting--

In Column 8, line 32: "bases;)" should read --bases)--

In Column 9, line 39: "genoine" should read --genome--

In Column 10, line 11: "And" should read --and--

In Column 10, line 17: "USP" should read --USA--

In Column 11, line 12: "biocidie" should read --biocide--

In Column 15, line 65: under "Parent 1" column the last entry "Rf2]" should read --rf2]--

In Column 16, line 66: "B z1" should read --Bz1--

In Column 18, line 12: "egt II" should read --Bgl II--

UNITED STATES PATENT AND TRADEMARK OFFICE
CERTIFICATE OF CORRECTION

PATENT NO. : 5,981,833
DATED : November 9, 1999
INVENTOR(S) : Roger P. Wise; Patrick S. Schnable It is certified that errors appear in the above-identified patent and that said Letters Patent is hereby corrected as shown below:

In Column 22, line 67: "SEQ ID NO:4" should read --[SEQ ID NO:4]--

IN THE CLAIMS:

In Claim 16, Column 35, line 17: "Rf1" should read --Rf2--

Signed and Sealed this

First Day of August, 2000

Q. TODD DICKINSON

*Attest:*

*Attesting Officer*    *Director of Patents and Trademarks*